US011832928B2

(12) United States Patent
Kingsford

(10) Patent No.: US 11,832,928 B2
(45) Date of Patent: Dec. 5, 2023

(54) HEART FAILURE INDICATOR

(71) Applicant: Impedimed Limited, Pinkenba (AU)

(72) Inventor: Catherine Anne Kingsford, Wavell Heights (AU)

(73) Assignee: IMPEDIMED LIMITED, Pinkenba (AU)

(*) Notice: Subject to any disclaimer, the term of this patent is extended or adjusted under 35 U.S.C. 154(b) by 1266 days.

(21) Appl. No.: 15/999,048

(22) PCT Filed: Feb. 15, 2017

(86) PCT No.: PCT/AU2017/050128
§ 371 (c)(1),
(2) Date: Aug. 16, 2018

(87) PCT Pub. No.: WO2017/139839
PCT Pub. Date: Aug. 24, 2017

(65) Prior Publication Data
US 2019/0357804 A1    Nov. 28, 2019

Related U.S. Application Data

(60) Provisional application No. 62/295,967, filed on Feb. 16, 2016.

(51) Int. Cl.
*A61B 5/0537* (2021.01)
*A61B 5/02* (2006.01)
*A61B 5/00* (2006.01)

(52) U.S. Cl.
CPC ........ *A61B 5/0537* (2013.01); *A61B 5/02028* (2013.01); *A61B 5/4875* (2013.01);
(Continued)

(58) Field of Classification Search
CPC . A61B 5/0537; A61B 5/02028; A61B 5/4875; A61B 5/4881; A61B 5/4842; A61B 5/7275
See application file for complete search history.

(56) References Cited

U.S. PATENT DOCUMENTS 5,788,643 A * 8/1998 Feldman .............. A61B 5/4869
128/898
8,374,688 B2 * 2/2013 Libbus ................. A61B 5/0537
600/547
(Continued)

FOREIGN PATENT DOCUMENTS

EP           2319411 A2 *  5/2011  ......... A61B 5/02028
WO   WO-2008064426 A1 *  6/2008  ........... A61B 5/0537
(Continued)

OTHER PUBLICATIONS

International Search Report and Written Opinion dated May 3, 2017 for Application No. PCT/AU2017/050128.
(Continued)

*Primary Examiner* — Sean P Dougherty
(74) *Attorney, Agent, or Firm* — Knobbe, Martens, Olson & Bear, LLP

(57) ABSTRACT

System for determining heart failure indicator indicative of a heart failure disease state in a subject, including processing device(s) that at least in part control signal generator(s) and receives an indication of a measured response signal from sensor(s) allowing first and second impedance measurement (s) to be performed across at least one body segment, determines a first fluid level indicator using first impedance value(s) obtained by performing the first impedance measurement(s), the first fluid indicator being indicative of a first ratio of ECF to TBW at a first time, determines a second fluid level indicator using second impedance value(s) obtained by performing the second impedance measurement (s), the second fluid indicator being indicative of a second ratio of ECF to TBW at a second time, determines a fluid level change using a difference in the first and second fluid level indicators, and, determines the heart failure indicator using the fluid level change.

21 Claims, 18 Drawing Sheets

(52) U.S. Cl.
CPC .......... *A61B 5/6823* (2013.01); *A61B 5/6832* (2013.01); *A61B 5/4881* (2013.01); *A61B 5/7203* (2013.01); *A61B 5/7225* (2013.01)

(56) References Cited

U.S. PATENT DOCUMENTS

| | | | | |
|---|---|---|---|---|
| 8,412,317 | B2* | 4/2013 | Mazar | A61B 5/282 600/547 |
| 8,460,189 | B2* | 6/2013 | Libbus | A61B 5/4869 600/386 |
| 8,718,752 | B2* | 5/2014 | Libbus | A61B 5/7275 600/515 |
| 8,744,564 | B2* | 6/2014 | Ward | A61B 5/0537 600/547 |
| 8,761,870 | B2* | 6/2014 | McGree | A61B 5/053 600/547 |
| 8,790,259 | B2* | 7/2014 | Katra | A61B 5/746 600/301 |
| 8,897,868 | B2* | 11/2014 | Mazar | A61N 1/36521 600/386 |
| 9,411,936 | B2* | 8/2016 | Landrum | A61B 5/02405 |
| 9,504,406 | B2* | 11/2016 | Chetham | A61B 5/0537 |
| 9,615,767 | B2* | 4/2017 | Gaw | A61B 5/0537 |
| 9,955,916 | B2* | 5/2018 | Bonomi | A61B 5/6823 |
| 2005/0039763 | A1* | 2/2005 | Kraemer | A61B 5/0537 128/920 |
| 2007/0273504 | A1* | 11/2007 | Tran | A61B 5/0295 340/539.12 |
| 2009/0043222 | A1* | 2/2009 | Chetham | G16H 50/30 600/547 |
| 2009/0143663 | A1* | 6/2009 | Chetham | A61B 5/4878 600/372 |
| 2011/0245711 | A1 | 10/2011 | Katra et al. | |
| 2014/0249384 | A1* | 9/2014 | Levin | A61B 5/4839 600/300 |
| 2015/0068069 | A1* | 3/2015 | Tran | A43B 3/34 340/693.1 |
| 2015/0374256 | A1* | 12/2015 | Skrabal | A61B 5/0535 600/301 |
| 2016/0015276 | A1 | 1/2016 | Strauss et al. | |
| 2016/0287166 | A1* | 10/2016 | Tran | A61B 5/74 |
| 2017/0042448 | A1* | 2/2017 | Dovancescu | A61B 5/0537 |

FOREIGN PATENT DOCUMENTS

| | | | | |
|---|---|---|---|---|
| WO | WO 2013/090798 | A1 | 6/2013 | |
| WO | WO 2013/182985 | A1 | 12/2013 | |
| WO | WO-2014128237 | A1 * | 8/2014 | ............. A61B 5/029 |
| WO | WO-2015169911 | A1 * | 11/2015 | ........... A61B 5/0537 |

OTHER PUBLICATIONS

International Preliminary Report on Patentability dated Aug. 21, 2018 for Application No. PCT/AU2017/050128.

* cited by examiner

HEART FAILURE INDICATOR

RELATED APPLICATIONS

This application is a U.S. National Phase under 35 U.S.C. 371 of the International Patent Application No. PCT/AU2017/050128, filed Feb. 15, 2017, and published in English on Aug. 24, 2017 as WO 2017/139839, which claims the benefit of U.S. Provisional Application No. 62/295,967, filed Feb. 16, 2016, each of which is incorporated by reference in its entirety.

BACKGROUND OF THE INVENTION

The present invention relates to a method and system for use in determining a heart failure indicator, for use in assisting diagnosis and monitoring of heart failure in a biological subject.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Congestive heart failure (CHF) causes difficulty breathing because oxygen exchange in the lung is impeded by pulmonary congestion. The vast majority of CHF hospital admissions are because of difficulty breathing. Further, the high rate of CHF readmission (by some estimates approximately 24% within 30 days) is due to re-accumulation or inadequate removal of pulmonary congestion resulting in difficulty breathing. Currently, there is no quantifiable method or metric to identify pulmonary congestion and better prevent difficulty breathing and hospital admission. This problem is growing. In 2010, there was an estimated 5.8 million CHF cases in the US, with over 670,000 new cases each year.

A subject suffering from CHF may be diagnosed using a physical exam and various imaging techniques to image the subject's chest. Treatment typically includes the use of vasodilators (e.g., ACEI/ARB), beta blockers, and diuretic therapy (e.g., Lasix). Management of treatment often proves difficult and unsuccessful. In particular, diuretic therapy is difficult for subjects and physicians to optimally manage. For example, changes in diet may require frequent changes in the diuretic therapy. Overuse (an underuse) of diuretic therapy may negatively impact clinical outcomes.

Pulmonary congestion is typically the result of high pulmonary blood pressures that drive fluid into the extravascular "spongy" interstitial lung tissue. High pulmonary blood pressures are present in subjects with elevated intravascular filling pressures as a result of heart failure. This high pulmonary blood pressure may also lead to increased amounts of fluid entering the extravascular space. Congestion within the extravascular interstitial lung tissue may prevent gas exchange ultimately, leading to a difficulty breathing that may require hospitalization. Hospital therapies are typically directed at reducing the pulmonary blood pressure by removing intravascular fluid with diuretic therapy. Although subject symptoms may improve, significant extravascular interstitial fluid may still be present. Subjects may feel well enough for discharge, but only a small change in pulmonary blood pressures will cause fluid to quickly re-accumulate, requiring readmission. Thus, subject symptoms do not reflect adequate treatment for the extent of the disease. Therefore, there is a need to detect and monitor extravascular interstitial fluid (e.g., lung wetness) and to provide an index or measure of the level extravascular interstitial fluid both instantaneously, and over time.

Currently, pulmonary congestion is typically monitored using a system such as CaridoMEMS™, which features a sensor that is placed in a subject's pulmonary artery to measure and monitor pulmonary artery pressure and heart rate. However, such a system is invasive and hence not easily deployed, and is therefore typically only used for ongoing monitoring as opposed to early stage diagnosis. Additionally, such a technique relies on increases in pulmonary artery pressure, which may only arise after significant build-up of fluid on the lungs, meaning significant intervention is typically required by the time worsening of heart failure is detected.

There are several methods for assessing total body water, as the most prominent indicator of hydration status, including methods based on bioelectrical impedance and conductance. For example, U.S. Pat. No. 4,008,712 to Nyboer discloses method and apparatus for performing electrical measurement of body electrical impedances to determine changes in total body water in normal and deranged states of the body, U.S. Pat. No. 5,615,689 to Kotler discloses a method of predicting body cell mass using impedance analysis, U.S. Pat. No. 6,280,396 to Clark discloses an apparatus and method for measuring subject's total body water content by measuring the impedance of the body, and U.S. Pat. No. 6,459,930 to Takehara et al. discloses a dehydration condition judging apparatus by measuring bio-electric impedance. However, these methods and systems have proven unreliable and difficult to implement. The aqueous tissues of the body, due to their dissolved electrolytes, are the major conductors of an electrical current, whereas body fat and bone have relatively poor conductance properties. Significant technical problems have hampered many such electrical methods for in vivo body composition analyses; impedance spectroscopy is an attempt to refine bio-impedance measurements, which measures resistance and reactance over a wide range of frequencies. A technique based on this approach is described in U.S. Pat. No. 6,125,297 to Siconolfi which describes a method and apparatus for determining volumes of body fluids in a subject using bioelectrical response spectroscopy.

There is therefore a need for a simple and highly accurate method and device for monitoring tissue hydration status that can be used in a broad range of field conditions.

SUMMARY OF THE PRESENT INVENTION

In one broad form an aspect of the present invention seeks to provide a system for determining a heart failure indicator indicative of a heart failure disease state in a biological subject, the system including: at least one signal generator coupled to first electrodes provided in electrical contact with the subject in use, the at least one signal generator being adapted to generate a drive signal; at least one sensor coupled to second electrodes provided in electrical contact with the subject in use, the at least one sensor being adapted to measure a response signal; and, at least one processing device that: at least in part controls the at least one signal generator and receives an indication of a measured response signal from the at least one sensor, allowing at least one first and second impedance measurement to be performed across at least one body segment of the subject; determines a first fluid level indicator using at least one first impedance value obtained by performing the at least one first impedance measurement, the first fluid indicator being indicative of a first ratio of extracellular fluid levels to total body water at a first time; determines a second fluid level indicator using at least one second impedance value obtained by performing the at least one second impedance measurement, the second fluid indicator being indicative of a second ratio of extracellular fluid levels to total body water at a second time; determines a fluid level change using a difference in the first and second fluid level indicators; and, determines the heart failure indicator using the fluid level change.

In one embodiment the first and second electrodes are spaced apart metal plates.

In one embodiment the electrodes are mounted on a housing configured to allow the subject to position their hands in contact with the housing and thereby form an electrical contact with the first and second electrodes.

In one embodiment the electrodes are mounted on a housing configured to allow the subject to position their feet in contact with the housing and thereby form an electrical contact with the first and second electrodes.

In one embodiment the system includes: four signal generators, each signal generator being electrically connected to a respective drive electrode; and, four sensors, each sensor being electrically connected to at least one of the sense electrodes to measure a response signal in the subject.

In one embodiment the at least one processing device selectively controls the four signal generators and four sensors to perform a sequence of impedance measurements, the impedance measurements including at least one of: segmental impedance measurements; and, whole of body impedance measurements.

In one embodiment the at least one processing device: determines a rate of change of the fluid level change; and, determines the heart failure indicator using the rate of change.

In one embodiment the at least one processing device: compares the rate of change to at least one threshold; and, determines the heart failure indicator in accordance with results of the comparison.

In one embodiment the at least one processing device: compares the fluid level change to at least one absolute reference; compares the rate of change to at least one rate of change reference; and, determines the heart failure indicator in accordance with results of the comparisons.

In one embodiment the at least one processing device: compares the fluid level change to at least one threshold; and, determines the heart failure indicator in accordance with results of the comparison.

In one embodiment the at least one threshold is based on at least one of: a threshold or variance established for a sample reference population; and, a time period between the first and second time.

In one embodiment the at least one processing device: determines trends in the fluid level changes; and, determines the heart failure indicator in accordance with the trends.

In one embodiment the at least one processing device: determines a fluid level gradient using the fluid level change and the first and second times; and, determines the heart failure indicator using the fluid level gradient.

In one embodiment the at least one processing device determines at least one of a degree and a severity of heart failure in accordance with the heart failure indicator.

In one embodiment the system includes a display, and the at least one processing device: generates a representation using at least one of the fluid level change and the heart failure indicator, and, displays the representation on the display.

In one embodiment the at least one processing device: determines a baseline using the first fluid level indicator; determines a plurality of second fluid level indicators by performing multiple impedance measurements at subsequent times; determines a plurality of fluid level changes using a difference in the baseline and each of the plurality of second fluid level indicators; and, determines the heart failure indicator using the plurality of fluid level changes.

In one embodiment the body segment includes at least one of: a torso of the subject; a lower extremity of the subject; a limb of the subject; a part of a limb of the subject; and, a whole body of the subject.

In one broad form an aspect of the present invention seeks to provide a system for determining a heart failure indicator indicative of a heart failure disease state in a biological subject, the system including: at least one signal generator coupled to first electrodes provided in electrical contact with the subject in use, the at least one signal generator being adapted to generate a drive signal; at least one sensor coupled to second electrodes provided in electrical contact with the subject in use, the at least one sensor being adapted to measure a response signal; and, at least one processing device that: at least in part controls the at least one signal generator and receives an indication of a measured response signal from the at least one sensor, allowing at least one impedance measurement to be performed across at least one body segment of the subject; determines a fluid level indicator using at least one impedance value obtained by performing the at least one impedance measurement; and, determines a heart failure indicator using the fluid level indicator.

In one embodiment the fluid level indicator is at least partially indicative of at least one of: extracellular fluid levels in the body segment; intracellular fluid levels in the body segment; total body water; a ratio of extracellular fluid levels in the body segment to total body water; a ratio of extracellular to intracellular fluid levels in the body segment; and, a ratio of intracellular to extracellular fluid levels in the body segment.

In one embodiment the body segment includes at least one of: a torso of the subject; a lower extremity of the subject; a limb of the subject; a part of a limb of the subject; and, a whole body of the subject.

In one embodiment the at least one processing device: determines a first fluid level indicator using at least one first impedance value obtained by performing at least one impedance measurement across at least a body segment of the subject at a first time; determines a second fluid level indicator using at least one second impedance value obtained by performing at least one impedance measurement across at least a body segment of the subject at a second time; and, determines the heart failure indicator using the first and second fluid level indicators.

In one embodiment the at least one processing device: determines a fluid level change using a difference in the first and second fluid level indicators; and, determines the heart failure indicator using the fluid level change.

In one embodiment the at least one processing device: determines a rate of change of the fluid level change; and, determines the heart failure indicator using the rate of change.

In one embodiment the at least one processing device: compares the rate of change to at least one threshold; and, determines the heart failure indicator in accordance with results of the comparison.

In one embodiment the at least one processing device: compares the fluid level change to at least one threshold; and, determines the heart failure indicator in accordance with results of the comparison.

In one embodiment the at least one threshold is based on at least one of: a threshold or variance established for a sample reference population; and, a time period between the first and second time.

In one embodiment the at least one processing device: determines trends in the fluid level changes; and, determines the heart failure indicator in accordance with the trends.

In one embodiment the at least one processing device: determines a peak fluid level indicator indicative of a peak in the trends; determines a time period associated with the peak fluid level indicator, and, determines the heart failure indicator in accordance with the time period.

In one embodiment the at least one processing device: determines a nadir fluid level indicator indicative of a nadir in the trends; determines a time period associated with the nadir fluid level indicator; and, determines the heart failure indicator in accordance with the time period.

In one embodiment the at least one processing device: determines a fluid level gradient using the first and second fluid level indicators and the first and second times; and, determines the heart failure indicator using the fluid level gradient.

In one embodiment the at least one processing device: compares the fluid level change to at least one absolute reference; compares the rate of change to at least one rate of change reference; and, determines the heart failure indicator in accordance with results of the comparisons.

In one embodiment the at least one processing device: determines a baseline using the first fluid level indicator; determines a plurality of second fluid level indicators by performing multiple impedance measurements at subsequent times; determines a plurality of fluid level changes using a difference in the baseline and each of the plurality of second fluid level indicators; and, determines the heart failure indicator using the plurality of fluid level changes.

In one embodiment the at least one processing device determines at least one of a degree and a severity of heart failure in accordance with the heart failure indicator.

In one embodiment the system includes a display, and the at least one processing device: generates a representation using at least one of the fluid level indicator and the heart failure indicator, and, displays the representation on the display.

In one embodiment the at least one processing device: determines at least one impedance parameter value using at least one of: an impedance value obtained by performing impedance measurements at a single frequency; and, a plurality of impedance values obtained by performing impedance measurements at a plurality of frequencies; and, determines the fluid level indicator using the at least one impedance parameter value.

In one embodiment the impedance parameter values include at least one of: $R_0$ which is the resistance at zero frequency; $R_\infty$ which is the resistance at infinite frequency; and, $Z_c$ which is the resistance at a characteristic frequency.

In one embodiment the at least one processing device: uses the fluid level indicator to determine further analysis to be performed; performs the further analysis to determine one or more further fluid level indicators; and, determines the heart failure indicator at least partially in accordance with the further fluid level indicators.

In one embodiment the further analysis includes: determining further impedance measurements to be performed; causing the further impedance measurements to be performed; and, determining the further fluid level indicator using the further impedance measurements.

In one embodiment the at least one processing device: uses the fluid level indicator to identify a plurality of possible disease states; identifies further analysis to be performed in accordance with the identified possible disease states; and, performs the further analysis to thereby distinguish between the possible disease states and heart failure.

In one embodiment the at least one processing device: determines a signature indicative of a plurality of fluid level indicators; and, compares the signature to at least one of: a reference signature derived from a reference population; and, a previous signature for the subject; and, determines the heart failure indicator in accordance with results of the comparison.

In one embodiment the signature is indicative of two or more of: a torso fluid level indicator; at least one body segment fluid indicator, the body segment being a body segment other than the torso; and, a difference between a torso fluid level indicator and a body segment fluid indicator.

In one embodiment the at least one processing device: determines a signature indicative of: at least one fluid level indicator; and, at least one other subject body parameter value obtained by performing at least one measurement on one or more other body parameters of the subject; compares the signature to at least one of: a reference signature derived from a reference population; and, a previous signature for the subject; and, determines the heart failure indicator in accordance with results of the comparison.

In one embodiment the at least one other subject body parameter value is indicative of at least one of: a vital signs indicator, a cardiac parameter value; a respiratory parameter value; a blood potassium level; a temperature; a blood pressure; a respiratory rate; a heart rate; and, a blood oxygenation level.

In one embodiment the at least one processing device: determines selected reference signatures using subject characteristic data indicative of one or more physical characteristics of the subject; compares at least the subject impedance indicators to the selected reference signatures; and, generates the heart failure indicator at least partially in accordance with results of the comparison.

In one embodiment the at least one processing device: generates at least one subject signature indicative of the at least one fluid level indicator and at least one other subject body parameter value; and, compares the at least one subject signature to the selected reference ranges.

In one embodiment the at least one processing device generates the heart failure indicator based on a degree of similarity between the subject signature and the selected reference signatures.

In one embodiment the system includes a measuring unit including: the at least one signal generator coupled to the first electrodes provided in electrical contact with the subject in use; the at least one sensor coupled to the second electrodes provided in electrical contact with the subject in use; and, a measuring device processor that at least in part controls the at least one signal generator and receives an indication of a measured response signal from the at least one sensor, allowing the at least one impedance measurement to be performed.

In one embodiment the system is adapted to perform an arm-to-arm torso measurement and includes: the first electrodes positioned on the arms or hands of the subject; and, the second electrodes positioned on the arms or hands of the subject.

In one embodiment the system is adapted to perform a torso measurement and includes: the first electrodes positioned on hand and foot on a unilateral side of the body; and, the second electrodes positioned on hand and foot on a contralateral side of the body.

In one embodiment the electrodes are mounted on a housing configured to allow the subject to position their hands in contact with the housing and thereby form an electrical contact with the first and second electrodes.

In one embodiment the electrodes are mounted on a housing configured to allow the subject to position their feet in contact with the housing and thereby form an electrical contact with the first and second electrodes.

In one embodiment the impedance measuring unit includes: a measuring device including: the at least one signal generator; the at least one sensor; the measuring device processor; and, a first connector electrically connected to the at least one sensor and the at least one signal generator; and, a connectivity module including: the electrodes; and, a second connector electrically connected to the electrodes, wherein in use the measuring device is connected to the connectivity module by interconnecting the first and second connectors so that first electrodes are electrically connected to the at least one signal generator and second electrodes are electrically connected to the at least one sensor, thereby allowing the drive signal to be applied to the reference individual via the first electrodes and allowing the response signal to be measured via the second electrodes so that the at least one impedance measurement can be performed.

In one embodiment the measuring device is adapted to be used with a number of different connectivity module types, and wherein the measuring device processor performs the at least one impedance measurement at least in part depending on the connectivity module type of a connected connectivity module.

In one embodiment each measuring system includes a processing system in communication with the measuring unit, the processing system including the at least one processing device and being configured to: cause impedance measurements to be performed by the measuring unit; and, determine the heart failure indicator.

In one embodiment the processing system: determines an impedance measurement process to be performed, the impedance measurement process including a sequence of impedance measurements; causes the measuring unit to perform the sequence of impedance measurements; receives an indication of at least one impedance value from the measuring unit, the at least one impedance value being indicative of a measured impedance; and, generates impedance data using the at least one impedance value.

In one embodiment the at least one processing device determines the fluid level indicator using an average of the at least one impedance values.

In one broad form an aspect of the present invention seeks to provide a method for determining a heart failure indicator indicative of a heart failure disease state in a biological subject, the method including, in at least one processing device: determining a first fluid level indicator using at least one first impedance value obtained by performing at least one first impedance measurement across at least one body segment of the subject, the first fluid indicator being indicative of a first ratio of extracellular fluid levels to total body water at a first time; determining a second fluid level indicator using at least one sound impedance value obtained by performing at least one second impedance measurement across the at least one body segment, the second fluid indicator being indicative of a second ratio of extracellular fluid levels to total body water at a second time; determining a fluid level change using a difference in the first and second fluid level indicators; and, determining the heart failure indicator using the fluid level change.

In one broad form an aspect of the present invention seeks to provide a method for determining a heart failure indicator indicative of a heart failure disease state in a biological subject, the method including, in at least one processing device: determining a fluid level indicator using at least one impedance value obtained by performing at least one impedance measurement across at least a body segment of the subject; and, determining a heart failure indicator using the fluid level indicator.

In one broad form an aspect of the present invention seeks to provide a method of monitoring heart failure in a biological subject, the method including: periodically performing at least one impedance measurement across at least a torso of a subject deemed susceptible to heart failure to determine at least one impedance value; for each measurement, determining a fluid level indicator using the at least one impedance value; monitoring changes in the fluid level indicator over time; and, determining a heart failure indicator using the monitored changes.

In one broad form an aspect of the present invention seeks to provide a method for treating a heart failure disease state in a biological subject, the method including, in at least one processing device: determining a fluid level indicator using at least one impedance value obtained by performing at least one impedance measurement across at least a body segment of the subject; determining a heart failure indicator using the fluid level indicator; selecting a treatment based upon the heart failure indicator; and, causing the treatment to be administered over time to thereby at least partially treat the heart failure disease state of the subject.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
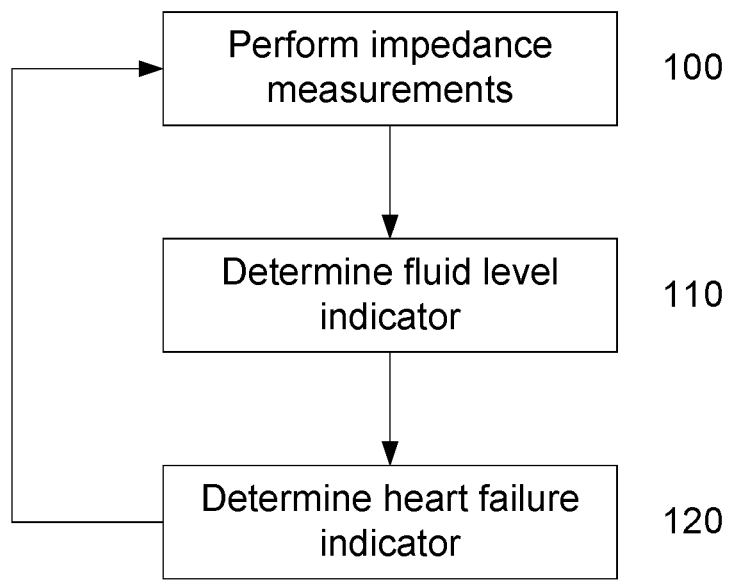
FIG. 1 is a flowchart of an example of a method for determining a heart failure indicator indicative of a heart failure state in a biological subject.

An example of a method for determining a heart failure indicator indicative of a heart failure state in a biological subject will now be described with reference to FIG. 1.

For the purpose of illustration, it is assumed that the following processes are performed at least in part using one or more electronic processing devices forming part of one or more processing systems, connected to one or more measuring systems, such as impedance measuring systems or the like. In one example, this is performed at least using a cloud based architecture that interfaces with measuring systems or other client devices located at multiple locations, as will be described in more detail below.

In this example, at step 100 impedance measurements are performed in order to determine at least one impedance value indicative of an impedance across at least a body segment of the subject. The impedance measurements can be performed in any appropriate manner and could be performed using a suitable impedance measurement device. Measured impedances can then be analysed by the impedance measurement device, or transferred to a remote processing device, such as a processing device in a client device, for further analysis. The impedance measurements can be performed using electrodes positioned on specific body segments of the subject, in order to measure a local impedance, but more typically are performed using electrodes positioned on the arms and/or hands of the subject. For example, when measuring the impedance of the torso, a drive signal is injected through the arms, causing the signal to pass through the torso, with a corresponding response signal also being measured through the arms. This configuration will hereinafter be referred to as an arm-to-arm measurement. In a further example, when measuring the impedance of the torso, a drive signal may be injected through a hand and foot on a unilateral side of the body, with a corresponding response signal being measured via sense electrodes positioned on the contralateral side, namely the hand and foot on the opposing side of the body. In this regard, a drive signal applied to the subject's left hand and foot, and sense electrodes positioned on the subject's right hand and foot, provides a measurement of the subject's left torso, and vice versa. Alternatively, measuring the impedance of the torso may include subtracting impedance measurements obtained of the limbs from an impedance measurement of the whole body. In a further alternative, the measurement could be a whole of body measurement, this incorporating a component based on the impedance of the torso and/or could be a measurement of one or more limbs, depending on the preferred implementation.

At step 110, the processing device uses the impedance value(s) to determine a fluid level indicator that is at least partially indicative of fluid levels in at least the body segment. The indicator could be of any appropriate form and could include a numerical value based on or derived from the impedance value(s). In one example, the fluid level indicator is simply an impedance value, but more typically is derived from multiple impedance measurements, analysed to determine a value indicative of fluid levels, such as intracellular fluid levels, extracellular fluid levels, or the like.

At step 120, the fluid level indicator is used to determine a heart failure indicator indicative of a heart failure state. In particular, this could encompass providing an indicator indicative of a presence, absence, degree or severity of heart failure, a likelihood the subject has heart failure, a prognosis associated with any heart failure, an indication of worsening heart failure, an indication of cardiac decompensation, or the like. The heart failure indicator could be determined in any suitable manner, such as by comparing the fluid level indicator to one or more references, and determining the heart failure indicator based on results of the comparison. Additionally, and/or alternatively, the fluid level indicator could be compared to previously determined fluid level indicators for the subject, to determine if there has been a change in fluid levels in the torso of the subject. In this regard, an increase in fluid levels can be indicative of an onset of, or an increase in the severity of, heart failure.

It will be appreciated that examining fluid levels in a body segment, such as the torso of the subject, can be used to identify increases in fluid levels, including in intracellular and/or extracellular fluid levels, which in turn can be indicative of the onset or worsening of heart failure and/or cardiac decompensation. The ability to monitor the fluid levels using impedance analysis, allows the fluid levels to be quantified to a high degree of accuracy, which in turn can be used to detect the unset or worsening of heart failure. Furthermore, this can be performed prior to clinical symptoms being detectable through other techniques, such as increased pulmonary artery pressure, shortness of breath, increased heart rate or the like, meaning this approach can detect the onset or worsening of heart failure at an earlier stage than existing techniques, allowing for more effective intervention.

Additionally, impedance measurements can be performed non-invasively using basic equipment, allowing this to be self-administered in a home environment without medical intervention. This in turn allows the technique to be applied more widely, and through more constant monitoring, can more effectively identify when medical intervention is required, leading to improved outcomes in heart failure management.

A number of further features will now be described.

In one example, the fluid level indicator is at least partially indicative of extracellular fluid levels in the body segment, intracellular fluid levels in the body segment, total body water, a ratio of extracellular fluid levels in the body segment to total body water, a ratio of extracellular to intracellular fluid levels in the body segment and/or a ratio of intracellular to extracellular fluid levels in the body segment. It will be appreciated that multiple fluid level indicators could be used, so intracellular and extracellular fluids could be monitored independently and in conjunction, which can assist in distinguishing between fluid level changes arising due to heart failure or other causes.

The body segments can include the torso and/or a limb(s) of the subject, a lower extremity of the subject, a part of a limb of the subject, as well as the entire body in the case of whole body impedance measurements. Whilst measurements can be of a single body segment, alternatively measurements can be made of multiple body segments, with the measurements across multiple body segments being used in conjunction in order to improve the effectiveness of the approach in determining an indicator indicative of heart failure.

The processing device can also be adapted to determine a first fluid level indicator using at least one first impedance value obtained by performing at least one impedance measurement across at least a body segment of the subject at a first time and then determine a second fluid level indicator using at least one second impedance value obtained by performing at least one impedance measurement across at least the body segment of the subject at a second time. Thus measurements can be separated in time, with the heart failure indicator being determined using the first and second fluid level indicators.

This approach can be used to determine a fluid level change using a difference in the first and second fluid level indicators and then determine the heart failure indicator using the fluid level change. This examines for changes in fluid levels in a body segment over time, allowing trends in fluid levels to be monitored. In some examples, a rate of change of the fluid level change may be determined, with the heart failure indicator being determined using the rate of change. For example these approaches can detect when fluid levels increase in the chest cavity or other body segment, hence indicating onset or worsening of heart failure. In this example, the at least one processing device can compare the fluid level change, and/or the rate of change, to at least one threshold and determine the heart failure indicator in accordance with results of the comparison. The threshold can be based on a threshold or variance established for a sample reference population and/or a time period between the first and second time. This allows the processing device to determine when a rate of fluid level increase exceeds an amount that would be expected in a healthy individual, or an individual without heart failure, thereby allowing the onset or worsening of heart failure to be identified.

Additionally or alternatively, the processing device may be adapted to compare the fluid level change to one or more absolute references, compare the rate of change to one or more rate of change references, and determine the heart failure indicator in accordance with the results of the comparison. The absolute and/or rate of change references may be established in any suitable manner, for example, similar to the process described in relation to the threshold above, and may include values, or ranges of values, or the like. For example, this arrangement allows for comparison of the both the level of fluid change, and the rate at which it is changing, to respective references, hence indicating worsening or an onset of heart failure based upon both a degree and speed at which fluid is accumulating in a body segment, such as the trunk.

It will be appreciated that whilst reference is only made to first and second times, in practice this could be extended, with multiple measurements being performed on a periodic basis, such as hourly, every 6 hours, twice daily, daily, twice weekly, weekly, monthly, substantially continuously or the like. This allows trends in fluid level changes to be monitored, for example to identify long term fluid level increases, which can in turn be assessed to identify the onset, progression and/or severity of heart failure.

In some examples, the processing device can also be adapted to determine a fluid level gradient using the first and second fluid level indicators and first and second times. For example, the gradient may include the fluid level change against a time change, or a ratio of fluid level change and time change, where the time change is a difference between the first and second times. Thus, the fluid level gradient may detect the speed of an increase in fluid levels in the chest cavity of other body segment, hence indicating a degree of worsening of heart failure.

Optionally, the processing device determines a degree and/or a severity of heart failure in accordance with the heart failure indicator. This may be achieved in any suitable manner including comparison of the fluid level indicator or heart failure indicator to a reference and determining a degree of similarity, which in turn provides a degree of the severity of heart failure. Alternatively, different reference ranges may correspond to differing degrees of heart failure, and thus severity may be determined by comparison of the indicator(s) to the respective reference ranges.

In another example, the processing device generates a representation using the fluid level indicator and/or the fluid level change and/or the heart failure indicator, and displays the representation on a display. The display may include any suitable display, for example, a display associated with the processing device or included in a system. Thus, results could be presented as a graphical representation, for example using a pointer and scale to indicate the likelihood of the subject having heart failure, the degree or severity of heart failure, or could include information regarding results of any comparisons, allowing a medical practitioner to understand the outcome of the analysis and how the heart failure indicator has been determined, which can facilitate the diagnostic or therapeutic process. For example, this could include displaying a graph showing multiple measurements separated over time, allowing medical practitioners to view trends in changes in fluid levels, using this to determine a degree or severity of heart failure.

In this regard, it will be appreciated that initial readings for the subject can be used as a baseline, effectively acting as a personalised reference baseline, with variations from the baseline being used to assess changes in the heart failure condition. Additionally, ongoing comparison to the references can be used to understand the impact of variations from the baseline, in particular understanding the degree to which the heart failure condition is worsening or improving, which can in turn be used to guide ongoing treatment. For example, the processing device may be adapted to determine a baseline using the first fluid level indicator at a first time, and determine a plurality of second fluid level indicators by performing multiple impedance measurements at subsequent times. A plurality of fluid level changes may then be determined using differences in the baseline and each of the second fluid level indicators, which can in turn be used to determine the heart failure indicator. As discussed above, the plurality of subsequent measurements may be performed sporadically, or on a periodic basis, such as hourly, every 6 hours, twice daily, daily, twice weekly, weekly, monthly, substantially continuously or the like.

In some examples, the processing device may also be adapted to determine a peak fluid level indicator and/or a nadir fluid level indicator indicative of a peak and/or a nadir in the trends, respectively. In this context "nadir" is typically used to refer to lowest or least. Whilst in some instances, the peak or the nadir may refer to a global peak or nadir in the trend(s), in other examples they include a localised peak or nadir, such that a trend may include multiple peaks and/or multiple nadirs.

In one embodiment the processing device determines a time period associated with the peak and/or nadir fluid level indicator, and determines the heart failure indicator in accordance with the time period. Accordingly, the time period may be indicative of the elapsed time to/from a baseline or predetermined time point to peak and/or nadir in the trend, such as a peak or nadir in fluid level indicators and/or fluid level changes. The baseline or predetermined time period may be associated with any suitable date/time and, for example, may include a hospital release date/time, a date/time of rehospitalisation, a predetermined time-of-day, or the like. Alternatively, the time period may be indicative of an elapsed time between the peak and the nadir, or vice versa, between peaks and/or between nadirs.

The fluid level indicators can be based on an impedance parameter value derived from one or more impedance measurements. For example, the processing device could determine one or more impedance parameter values using an impedance value obtained by performing impedance measurements at a single frequency or a plurality of impedance values obtained by performing impedance measurements at a plurality of frequencies: For example, a single low frequency measurement can be used to approximate $R_0$, which is the resistance at zero frequency, which is in turn indicative of extracellular fluid levels. Other parameters can include $R_\infty$, which is the resistance at infinite frequency $Z_c$, which is the resistance at a characteristic frequency. Thus, the impedance values could be measurements of impedance at one or more specific frequencies, with derived impedance parameter values corresponding to measurement of impedance at other frequencies, such as zero or infinite frequencies as will be appreciated by persons skilled in the art. Alternatively, the fluid level indicators could be based on fluid levels derived from impedance measurements, such as indications of extracellular fluid levels, intracellular fluid levels, or a ratio of the two.

The impedance measurements could be single frequency impedance measurements or could be performed at multiple frequencies as will be described in more detail below. The impedance measurements could be performed at any suitable frequency, but would typically include at least one low frequency measurement performed at less than 100 kHz and more typically about 30 kHz, and may also include one or more measurements at higher frequencies.

In one example, the processing device determines a torso fluid level indicator using at least one torso impedance value obtained by performing at least one impedance measurement across the torso of the subject and a segment fluid level indicator using at least one segmental impedance value obtained by performing at least one impedance measurement across a body segment of the subject, the body segment being a body segment other than the torso. Thus, separate fluid level indicators are obtained for the subject's torso and at least one other body segment. The heart failure indicator can then be determined using both the torso and segment fluid level indicators, for example by examining one or more of a difference in intracellular fluid levels between the torso and the body segment, a difference in extracellular fluid levels between the torso and the body segment and a difference in a ratio of intracellular to extracellular fluid levels between the torso and the body segment.

In this regard, it will be appreciated that in absence of heart failure, fluid levels in the chest and other segments of the body will typically have reasonably constant relative values. In the event that heart failure occurs, this will typically cause fluid to be redistributed, with fluid build-up occurring in different parts of the body. For example, in the case of congestive heart failure, this will typically cause a build-up of fluid in the chest cavity, meaning the torso fluid indicator will increase relative to fluid indicators for other body segments, such as the legs or arms. Conversely, a general change in hydration would typically alter fluid levels in all body segments. This in effect allows fluid levels in other body segments to act as controls to establish whether fluid level changes in the torso are indicative of heart failure.

It will be appreciated that the use of segmental analysis, to examine multiple different body segments, and ongoing monitoring to identify trends can be used in conjunction, for example to monitor for ongoing changes in fluid levels over time for two or more different body segments, typically including the torso and at least one other body segment. These can then be analysed independently, to assess changes in each body segment, or in conjunction to examine relative fluid level changes.

In one example, the processing device typically determines a first torso fluid level indicator using at least one first impedance value obtained by performing at least one impedance measurement across a torso of the subject at a first time and a first segmental fluid level indicator using at least one first impedance value obtained by performing at least one impedance measurement across a body segment of the subject at the first time, the body segment being a body segment other than the torso. The process device then determines a second torso fluid level indicator using at least one second impedance value obtained by performing at least one impedance measurement across at least a torso of the subject at a second time and a second segmental fluid level indicator using at least one second impedance value obtained by performing at least one impedance measurement across the body segment of the subject at the second time. Following this, the processing device determines a torso fluid level change using a difference in the first and second torso fluid level indicators and a segmental fluid level change using a difference in the first and second segmental fluid level indicators. The heart failure indicator can then be determined based on the torso and segmental fluid level changes. Thus, it will be appreciated that this process can identify changes in the torso and other body segment fluid levels over time. This can be used to examine trends in fluid levels in each body segment independently, but also track these changes relative to fluid level changes in other body segments, to see if the changes are localised to the torso.

Accordingly, in one example, the processing device determines a difference between the torso and segmental fluid level changes, compares the difference to a threshold and, determines the heart failure indicator in accordance with the difference. Alternatively, this can involve tracking trends in either or both of the torso and segmental fluid levels, using such trends to determine the heart failure indicator. For example, increases in both torso and limb fluid levels could be indicative of heart failure, with the degree and/or rate of change being indicative of a severity of heart failure.

It will further be appreciated that changes in fluid levels of one or more body segments alone may not be sufficient to adequately diagnose heart failure, for example as similar changes in fluid levels could arise for a number of different reasons. Accordingly, in one example, the processing device uses the fluid level indicator to determine further analysis to be performed, performs the further analysis to determine one or more further fluid level indicators and then determines the heart failure indicator at least partially in accordance with the further fluid level indicators.

For example, increases in fluid levels could be caused by pooling of blood as a result of other causes, such as venous insufficiency, changes in overall hydration or the like. Accordingly in one example, the process device uses the fluid level indicator to identify a plurality of possible disease states, and assuming one of these includes heart failure, then identifies further analysis that can be performed to distinguish between the identified possible disease states. The additional analysis is then performed to thereby distinguish between the possible disease states and heart failure.

The additional analysis could include simply performing further analysis of existing measurements, or may involve performing further impedance measurements, as required. For example, venous insufficiency is characterised by pooling of fluid in the legs, dependent on the orientation of the subject, in which case further measurements could be performed after the subject has undergone an orientation change, to help distinguish between venous insufficiency and heart failure.

It will be appreciated that instead of examining a single fluid level indicator, the system could alternatively examine multiple different fluid level indicators simultaneously. For example, this could involve monitoring extracellular fluid levels, intracellular fluid levels, relative fluid levels, with this being performed for the torso only, as well as the torso relative to other body segments.

When performing such an analysis, the processing device can determine a signature indicative of a plurality of different fluid level indicators and then compare the signature to at least one of a reference signature derived from a reference population and a previous signature for the subject, with the heart failure indicator being determined in accordance with the results of the comparison. In this example, two or more fluid level indicators, such as a torso fluid level indicator, a body segment fluid indicator, a difference between a torso fluid level indicator and a body segment fluid indicator, or the like, are combined into a single signature, with analysis then being performed relative to other similar signatures, so that each fluid level indicator is considered as part of the analysis.

Reference signatures can be derived from impedance measurements performed on reference individuals having different heart disease states and different physical characteristics. Groups of reference individuals having common heart failure states and physical characteristics can then be defined, with a reference signature for each group being established by examining distributions of different fluid level indicators of reference individuals within the group.

Thus, in generating the reference signatures, the processing device typically determines at least one heart failure state group, the heart failure state group being a group of reference individuals having a respective heart failure state, and then determines at least one reference signature for each heart failure state group using the Impedance indicators of the reference individuals within the heart failure state group. Accordingly, this process operates to segment the reference individuals into groups of individuals having certain heart failure states, then establishing a respective reference signature for individuals within that group.

Additionally, the processing device typically determines a plurality of characteristic groups, each characteristic group being a group of reference individuals having common physical characteristics. The processing device then determines at least one reference signature for each characteristic group using the impedance indicators of the reference individuals within the characteristic group. The characteristic groups are typically established as subgroups of the heart failure state groups, so that each heart failure state group is further divided into subgroups of individuals having respective physical characteristics. This allows the heart failure state to be identified by comparing the subject data measured for a particular subject to reference signatures established for individuals having similar physical characteristics thereby increasing the reliability of this process.

The reference signature could be of any appropriate form and could include defined values for absolute and/or relative values of impedance indicators obtained from one or more body segments, such as the torso. The reference signature could also include threshold values of impedance indicators or ranges or thresholds of changes in absolute or relative impedance indicators measured over defined time periods. Thus, each reference signature could therefore include a plurality of reference ranges, each reference range being based on at least one of a distribution of reference impedance indicators measured for a respective body segment, a distribution of differences in reference impedance indicators measured for different respective body segments and a distribution of impedance indicators measured at a specific times. However, this is not essential, and any suitable form of signature could be used.

In one example the reference signature is in the form of a multi-dimensional vector, with each row in the vector being indicative of a value or range of values for a respective fluid level indicator. In this instance, reference signatures are generated for multiple reference individuals in a reference population, with clustering of the reference signatures being performed on the basis of the severity of heart failure, and physical characteristics, allowing reference signatures to be established for different degrees of heart failure for individuals with common physical characteristics. For example, this could be performed using iterative global partitioning clustering algorithms and Bayesian evidence classification, support vector machines or the like, which can be used to effectively define decision boundaries in the multi-dimensional vector space.

In addition to using fluid levels, the system can also examine other body parameters. In this instance, a signature can be derived in a similar manner, with the signature being indicative of at least one fluid level indicator and at least one other body parameter value or indicator obtained by performing at least one measurement on one or more other body parameters of the subject. This allows a similar process to be performed to that described above, further taking to account other body parameters.

In this case, the other body parameters could be any body parameters, including but not limited to vital signs indicators, a cardiac parameter value, a respiratory parameter value, a blood potassium level, a fitness parameter, such as a number of steps walked, a temperature, a blood pressure, a respiratory rate, a heart rate, a blood oxygenation level, electrical activity of the heart (electrocardiography), subject weight, fat-free mass, fat mass, body mass index, or the like.

Thus, for example, the severity of heart failure might be different for given fluid levels if the subject has a high heart rate as opposed to a lower heart rate. The ability to define reference signatures based on impedance indicators as well as other body parameter values can assist in providing further improved discriminatory capabilities.

Once established reference signatures can be used in determining a heart failure indicator indicative of a likely heart failure state by comparing the signature to reference signatures. This process typically includes determining selected reference signatures using physical characteristics of the subject, comparing at least the subject impedance indicators to the selected reference signatures and generating the heart failure indicator at least partially in accordance with results of the comparison.

The comparison can be performed in any manner, and will for example depend on the nature of the reference signature. For example, if the reference signature is a multidimensional vector, then a similar subject signature vector can be created and compared using a suitable analysis technique, such as a Bayesian classification scheme or the like. The processing device can then generate the heart failure indicator based on a degree of similarity between the subject signature and the selected reference signatures, with the heart failure indicator being indicative of a likelihood of the subject having at least one heart failure state, for example based on the relative proximity of the subject signature and the reference signatures.

Optionally, the fluid level indicator is determined using an average of the impedance values. For example, two or more sequential impedance measurements may be performed in order to determine sequential impedance values, which are in turn averaged prior to further analysis. This may be advantageous in terms of increased accuracy and robustness of the resultant heart failure indicator.

The above described process can be performed repeatedly by periodically performing at least one impedance measurement across at least a torso, or body segment, of the subject to determine at least one impedance value, determining a fluid level indicator for each measurement, monitoring changes in the fluid level indicator over time and determining a heart failure indicator using the monitored changes.

Accordingly, it will be appreciated that the above described process can be performed on an ongoing basis, in order to monitor progression of a heart failure state. For example, performing repeated measurements for the subject, for example on a day-to-day or weekly basis, allows progression of heart failure states to be monitored. This in turn can significantly assist with long term management of chronic diseases.

For example, once diagnosed with chronic heart failure, a subject might repeat the measurement process in a home setting. In this instance, centralised analysis of the results can be used to identify if the subject's condition is worsening, in turn used to ensure early intervention is performed.

In this regard, it will be appreciated that initial readings for the subject can be used as a baseline, effectively acting as a personalised reference baseline signature, with variations from the baseline signature being used to assess changes in the condition. Additionally, ongoing comparison to the reference signatures can be used to understand the impact of variations from the baseline, in particular understanding the degree to which the condition or heart failure state is worsening or improving, and whether any secondary heart failure states are arising, which can in turn be used to guide ongoing treatment.

A further example of a method for determining a heart failure indicator indicative of a heart failure state in a biological subject will now be described with reference to FIG. 13.

In this example, at step 1300 first impedance measurements are performed in order to determine at least one first impedance value indicative of an impedance across at least a body segment of the subject. At step 1310, the processing device uses the first impedance value(s) to determine a first fluid level indicator that is indicative of a first ratio of extracellular fluid levels in a whole body to total body water at a first time.

At step 1320, second impedance measurements are performed in order to determine at least one second impedance value indicative of an impedance across at least a body segment of the subject. The processing device uses, at step 1330, the second impedance value(s) to determine a second fluid level indicator that is indicative of a second ratio of extracellular fluid levels in the whole body to total body water at a second time.

The first and second impedance measurements can be performed in any appropriate manner and could be performed using a suitable impedance measurement device, as discussed in any other example herein.

Additionally, the first and second fluid level indicators could be of any appropriate form and could include a numerical value based on or derived from the impedance value(s). Typically the extracellular fluid is indicative of the extracellular water in one or more body segments, whilst the total body water is indicative of fluid levels in the whole body of the subject. In one example, the first and second fluid level indicators are derived from multiple impedance measurements, analysed to determine a value indicative of the ratio of extracellular fluid and total body water, and this is discussed in more detail below.

Figure 13:
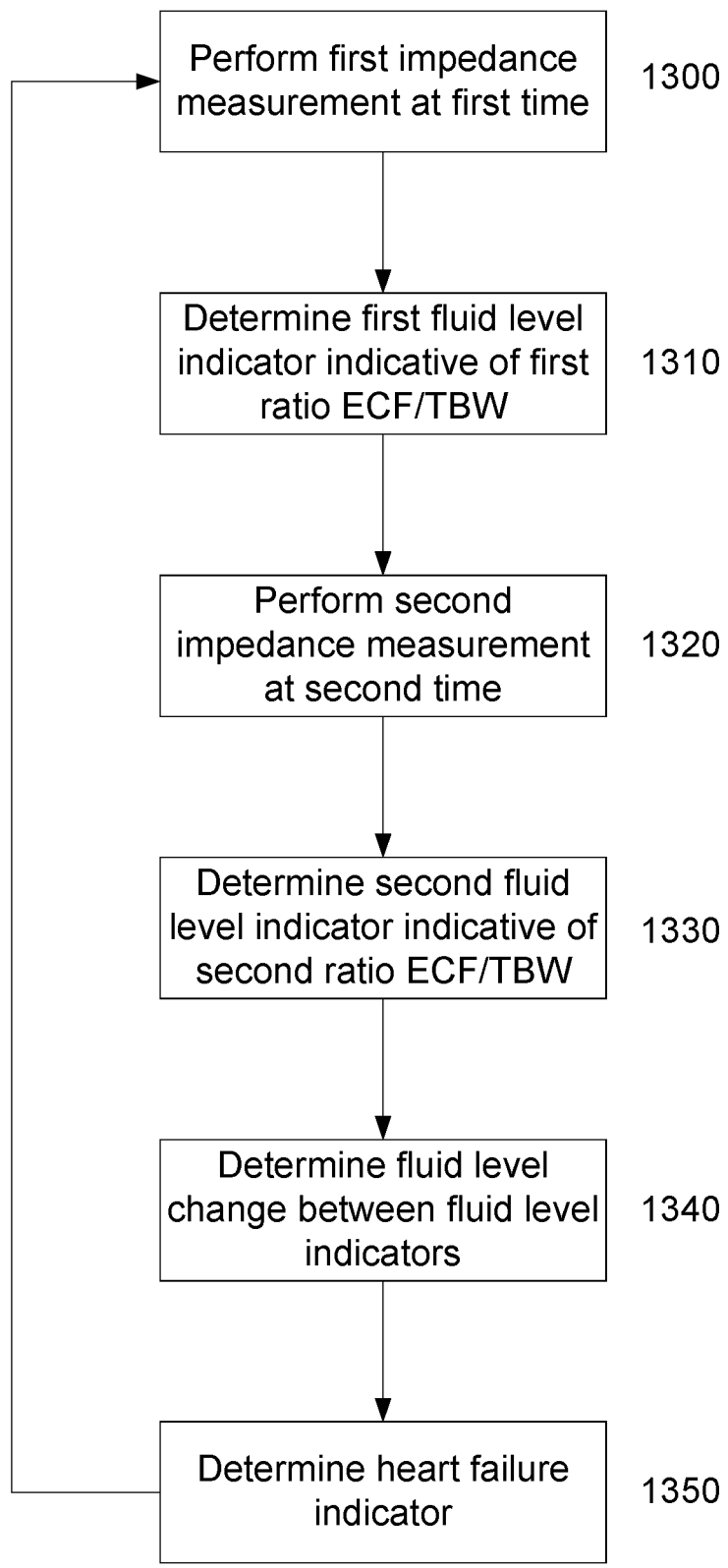
FIG. 13 is a flowchart of a further example of a method for determining a heart failure indicator indicative of heart failure status in a biological subject.

Moreover, steps 1310 and 1330 may be performed in any suitable order and may be performed as indicated in FIG. 13, after step 1320, or the like.

At step 1340, the processing system determines a fluid level change using a difference in the first and second fluid level indicators, and at step 1350 the fluid level change is used to determine a heart failure indicator indicative of a heart failure state.

As discussed above, this could encompass providing an indicator indicative of a presence, absence, degree or severity of heart failure, a likelihood the subject has heart failure, a prognosis associated with any heart failure, an indication of worsening heart failure, an indication of cardiac decompensation, or the like. The heart failure indicator could be determined in any suitable manner, such as by comparing the fluid level change to one or more references, and determining the heart failure change based on results of the comparison. Additionally, and/or alternatively, the fluid level change could be compared to previously determined fluid level changes for the subject, to determine if there has been a variance in fluid level changes in the subject.

Accordingly, the above described process may also be performed on an ongoing basis, in order to monitor progression of a heart failure state. For example, performing repeated measurements for the subject, for example on a day-to-day or weekly basis, allows progression of heart failure states to be monitored.

Moreover, this example process may incorporate any combination of any of the additional features described herein.

Figure 15:
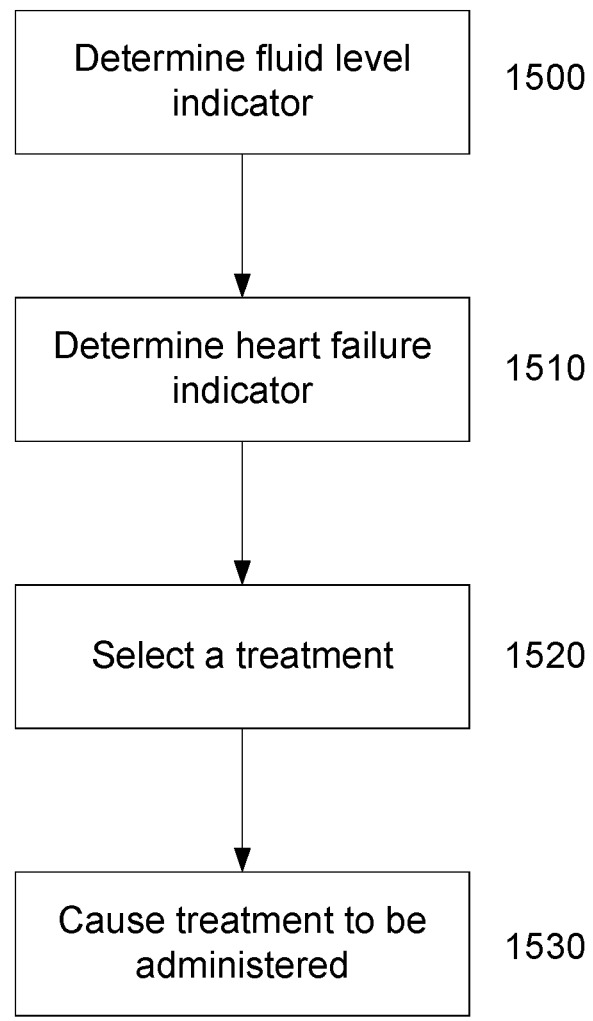

A further example of a method for treating a heart failure disease state in a biological subject will now be described with reference to FIG. 15.

In this example, at least one processing device determines, at step 1500, a fluid level indicator using at least one impedance value obtained by performing at least one impedance measurement across at least a body segment of the subject. This may be performed in any suitable manner including any of the examples described herein. The processing device determines a heart failure indicator using the fluid level indicator, at step 1510, and again this can be achieved in any suitable manner according to any of the examples described herein.

At step 1520 the processing device selects a treatment based upon the heart failure indicator. In this regard, the treatment may include any suitable treatment or therapy for heart failure, such as a prescription and/or dosage of vasodilators (e.g., ACEI/ARB), beta blockers, diuretic therapy (e.g., Lasix), prescriptive/proscriptive diet and/or exercise, and/or pacing therapy or pacing parameters, or the like.

At step 1530, the processing device causes the treatment to be administered over time to thereby at least partially treat heart failure/the heart failure disease state in the subject. Causing the treatment may include indirect causation, such as displaying, recording, or communicating the treatment parameters indicative of the treatment to allow a clinician and/or the subject to administer the treatment in accordance with the treatment parameters. For example, the treatment or treatment parameters indicative thereof, may be displayed on a display associated with the processing device allowing the subject to administer the treatment. In this regard, the treatment may include increasing or decreasing a dosage of vasodilators, beta blockers or the like, and accordingly the subject can self-administer the altered dose. Alternatively, the processing device may cause the treatment to be administered, for example, by causing pacing control signals to be applied to the patient, for example, via a pacing device, or the like.

Accordingly, the above described process may also be performed on an ongoing basis, in order to maintain treatment of heart failure. For example, performing repeated measurements for the subject, for example on a day-to-day or weekly basis, allows treatment of heart failure to be maintained. Beneficially, ongoing treatment allows for early detection and intervention in relation to worsening heart failure, which can decrease the incidence of hospitalisation, for example, due to cardiac decompensation.

Moreover, this example process may incorporate any combination of any of the additional features described herein.

These examples are thus particularly advantageous, as they provide a non-invasive and rapid method for performing an assessment of heart failure. This is beneficial for clinicians in providing frequent insight into a patient's heart failure status, which in turn are usable in informing adjustments to diuretic regimen and accelerating a return to euvolemia, thus preventing more severe symptoms, need for intravenous diuretics and potential hospitalisations.

Although not essential, in one example, the above described processes are implemented using a distributed architecture including one or more measuring systems in communication with one or more processing devices. An example system will now be described with reference to FIGS. 2 to 5.

In this example, the system 200 includes a number of measuring systems 210 coupled via a communications network 240 to one or more other measuring systems 210 and/or one or more processing devices, such as a server 250, which may in turn be coupled to a database 251. This arrangement allows data from performed measurements to be collected by the measurement systems 210 and provided to the server 250 for analysis. Collected data may also be stored in the database 251 together with resulting reference signatures and/or heart failure indicators, allowing this information to be remotely accessed and viewed by third parties, such as clinicians, or the like.

In the above arrangement, the communications network 240 can be of any appropriate form, such as the Internet and/or a number of local area networks (LANs) and provides connectivity between the measuring systems 210 and the server 250. It will however be appreciated that this configuration is for the purpose of example only, and in practice the measuring systems 210 and server 250 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

It will also be noted that the use of the distributed system is purely optional and the process can be implemented using a standalone measuring system.

Figure 3:
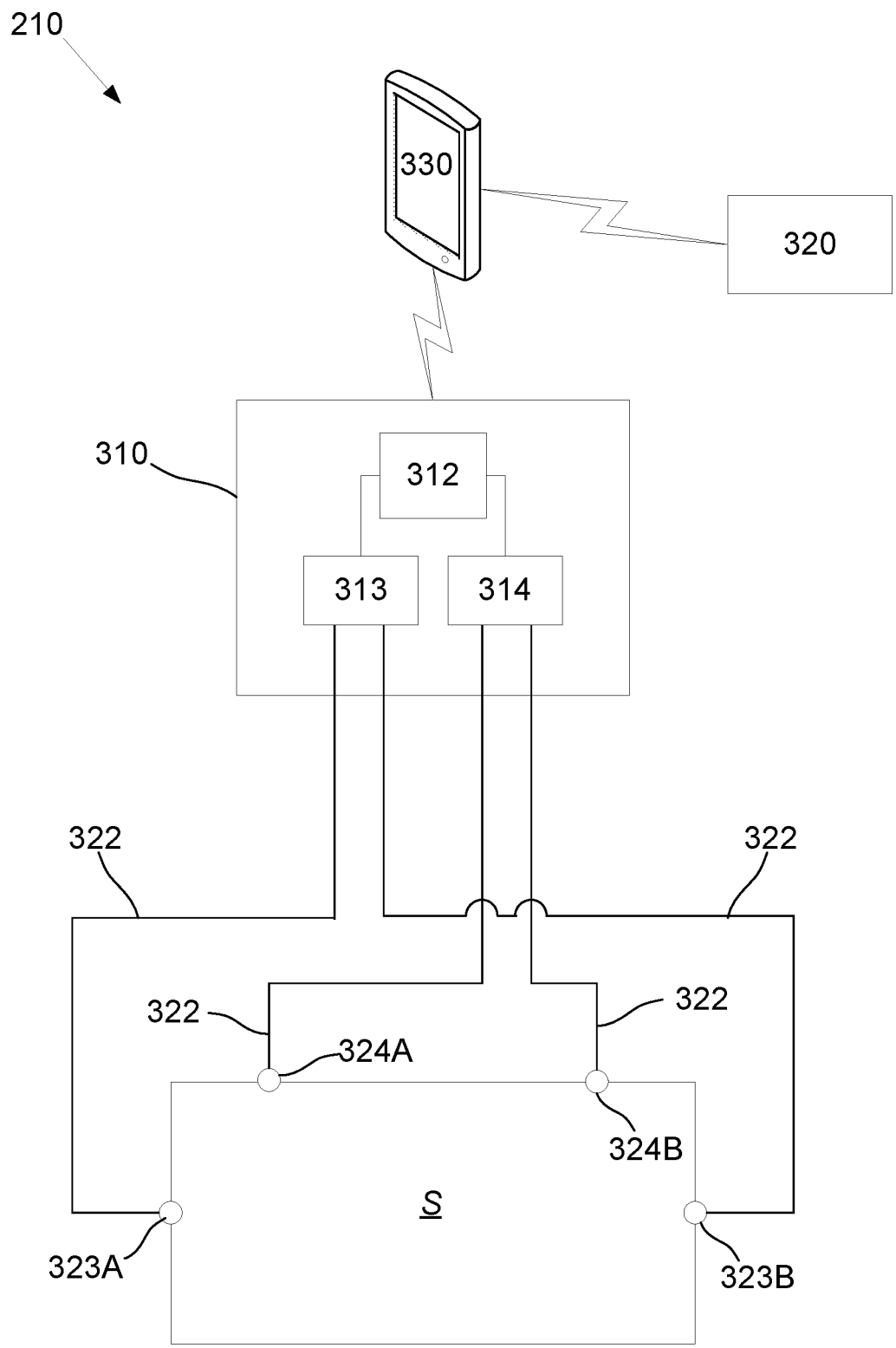
FIG. 3 is a schematic diagram of a measuring system.

An example measuring system will now be described in further detail with reference to FIG. 3.

In this example, the measuring system includes an impedance measuring unit having an impedance measuring device 310, which is in turn in communication with a processing system in the form of a client device 330, such as a portable computer system, mobile phone, tablet or the like. One or more optional physical characteristic sensors 320 can also be provided for capturing information regarding physical characteristics of an individual/subject.

The nature of the physical characteristic sensors 320 will vary depending on the characteristics to be measured, and could include for example scales for measuring an individual/subject's weight and/or an image capture device, such as a camera, body scanner, DEXA (Dual-Energy X-ray Absorptiometry), 3D laser or optical scanning, or the like, for measuring a height and/or body segment dimensions, as will be described in more detail below. Additionally or alternatively, this could include electronic scales for measuring a weight, and other monitoring equipment, for example for measuring heart rate, blood pressure or other characteristics.

The impedance measuring device 310 typically includes a measuring device processor 312 coupled to at least one signal generator 313 and at least one sensor 314, which are in turn coupled to respective drive and sense electrodes 323A, 323B and 324A, 324B, via leads 322. In use, the signal generator 313 generates a drive signal, which is applied to the individual/subject S via the drive electrodes 323A, 323B, whilst the sensor 314 measures a response signal via the sense electrodes 324A, 324B. In use, the measuring device processor 312 controls the at least one signal generator 313 and the at least one sensor 314, allowing the impedance measurements to be performed. The drive and sense electrodes 323A, 323B and 324A, 324B, may be provided in any suitable arrangement, and in one example, the drive and sense electrodes 323A, 323B and 324A, 324B, or first and second electrodes, are spaced apart metal plates. In this regard, in some examples, the electrodes 323A, 323B and 324A, 324B are mounted on a housing configured to allow the subject to position their hands and/or their feet in contact with the housing and thereby form an electrical contact with the first and second electrodes, or drive and sense electrodes 323A, 323B and 324A, 324B, and this will be described further below. However, this is not essential and in other examples the electrodes may include at least in part adhesive electrodes, or the like, which may be positioned in any suitable manner.

In particular, the measuring device processor 312 is adapted to generate control signals, which cause the signal generator 313 to generate one or more alternating signals, such as voltage or current signals of an appropriate wave-form, which can be applied to a subject S, via the first electrodes 323A, 323B and processing received signals from the sensor 314. It will be appreciated that the measuring device processor 312 may be any form of electronic processing device capable of performing appropriate control, and could include an FPGA (field programmable gate array), or a combination of a programmed computer system and specialised hardware, or the like.

The signal generator 313 could be of any appropriate form, but will typically include digital to analogue converters (DACs) for converting digital signals from the processing device to analogue signals, which are amplified to generate the required drive signals, whilst the sensor 314 typically includes one or more amplifiers for amplifying sensed response signals and analogue to digital converters (ADCs) to digitise the analogue response signals and providing digitised response signals to the processing device.

In one particular example, the system includes four signal generators 313, each signal generator 313 being electrically connected to a respective drive electrode, and four sensors 314, each sensor 314 being electrically connected to at least one of the sense electrodes 324A, 324B to measure a response signal in the subject. Optionally in this example, the measuring device processor 312 selectively controls the four signal generators and four sensors to perform a sequence of impedance measurements, the impedance measurements including segmental impedance measurements and/or whole of body impedance measurements. However, this is not essential and in other examples the system may include any suitable number of signal generators 313, sensors 314 and the like.

The nature of the alternating drive signal will vary depending on the nature of the measuring device and the subsequent analysis being performed. For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, commonly referred to as the impedance parameter value $R_0$, which is in turn indicative of extracellular fluid levels.

Alternatively, the applied signal can have a relatively high frequency, such as above 200 kHz, and more typically above 500 kHz, or 1000 kHz. In this instance, such high frequency signals can be used as an estimate of the impedance at infinite applied frequency, commonly referred to as the impedance parameter value $R_\infty$, which is in turn indicative of a combination of the extracellular and intracellular fluid levels, as will be described in more detail below.

Alternatively and/or additionally, the system can use Bioimpedance Spectroscopy (BIS) in which impedance measurements are performed at each of a number of frequencies ranging from very low frequencies (1 kHz and more typically 3 kHz) to higher frequencies (1000 kHz), and can use as many as 256 or more different frequencies within this range. Such measurements can be performed by applying a signal which is a superposition of a plurality of frequencies simultaneously, or a number of alternating signals at different frequencies sequentially, depending on the preferred implementation. The frequency or frequency range of the applied signals may also depend on the analysis being performed.

When impedance measurements are made at multiple frequencies, these can be used to derive one or more impedance parameter values, such as values of $R_0$, $Z_c$, $R_\infty$, which correspond to the impedance at zero, characteristic and infinite frequencies. These can in turn be used to determine information regarding both intracellular and extracellular fluid levels, as will be described in more detail below.

A further alternative is for the system to use Multiple Frequency Bioimpedance Analysis (MFBIA) in which multiple signals, each having a respective frequency are injected into the subject S, with the measured impedances being used in the assessment of fluid levels. In one example, four frequencies can be used, with the resulting impedance measurements at each frequency being used to derive impedance parameter values, for example by fitting the measured impedance values to a Cole model, as will be described in more detail below. Alternatively, the impedance measurements at each frequency may be used individually or in combination.

Thus, the measuring device 310 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with two signal generators 313 being independently controllable, to allow the signal voltage across the subject to be varied, for example to minimise a common mode signal and hence substantially eliminate any imbalance as described in copending patent application number WO2009059351.

As the drive signals are applied to the subject, the sensor 314 then determines the response signal in the form of the voltage across or current through the subject S, using second electrodes 324A, 324B. Thus, a voltage difference and/or current is measured between the second electrodes 324. In one example, a voltage is measured differentially, meaning that two sensors 314 are used, with each sensor 314 being used to measure the voltage at each second electrode 324 and therefore need only measure half of the voltage as compared to a single ended system. Digitised response signals are then provided to the measuring device processor 312, which determines an indication of the applied drive signal and measured response signals, and optionally uses this information to determine measured impedances.

In this regard, the response signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal may be demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise. Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined.

Thus, in the above arrangement, four electrodes are shown, with two forming drive electrodes and two forming sense electrodes. However, this is not essential, and any suitable number of electrodes could be used. Furthermore, a single signal generator and sensor are shown, but again a respective signal generator and sensor could be used for each drive and sense electrode, respectively, and the described arrangement is for the purpose of illustration only.

In the above arrangement, the client device 330 is coupled to the measuring device processor 312, allowing operation of the impedance measuring device to be controlled. In particular, the client device 330 can be used to instruct the measuring device processor 312 on a particular sequence of impedance measurements that need to be performed, further receiving either an indication of the drive/sense signals and/or measured impedance values. The client device 330 can then optionally perform further processing, for example to determine the impedance indicators, although alternatively this may not be required and raw impedance data could be provided to the server 250 for analysis.

The client device 330 can also combine impedance values or indicators with information regarding indications of heart failure states and physical characteristics determined either by manual user input or based on signals from one or more physical characteristic sensors. This allows the client device to generate the reference data, which is then transferred via the communications network 240 to the server 250. However, alternatively, the server 250 could obtain the indication of heart failure states and/or physical characteristic from other data sources, depending on the preferred implementation.

Figure 4:
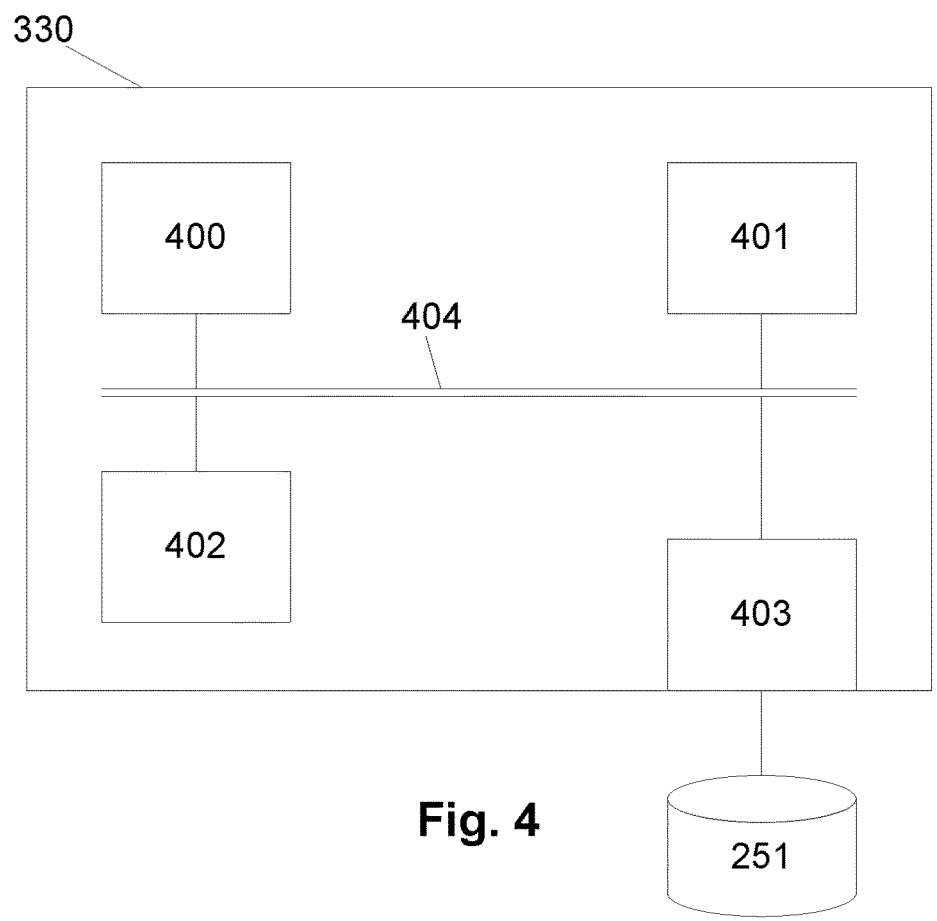
FIG. 4 is a schematic diagram of an example of a client device.

Accordingly, it will be appreciated that the client device 330 can be of any appropriate form and one example is shown in FIG. 4. In this example, the client device 330 includes at least one microprocessor 400, a memory 401, an input/output device 402, such as a keyboard and/or display, and an external interface 403, interconnected via a bus 404 as shown. The external interface 403 can be utilised for connecting the client device 330 to peripheral devices, such as the communications networks 240, databases, other storage devices, or the like. Although a single external interface 403 is shown, this is for the purpose of example only, and in practice multiple interfaces using various methods (eg. Ethernet, serial, USB, wireless or the like) may be provided.

In use, the microprocessor 400 executes instructions in the form of applications software stored in the memory 401 to allow communication with the server 250, for example to allow reference data to be provided to the sever, or the like.

Accordingly, it will be appreciated that the client device 330 may be formed from any suitable processing system, such as a suitably programmed PC, Internet terminal, laptop, or hand-held PC, and in one preferred example is either a tablet, or smart phone, or the like. Thus, in one example, the client device 330 is a standard processing system such as an Intel Architecture based processing system, which executes software applications stored on non-volatile (e.g., hard disk) storage, although this is not essential. However, it will also be understood that the client devices 330 can be any electronic processing device such as a microprocessor, microchip processor, logic gate configuration, firmware optionally associated with implementing logic such as an FPGA (Field Programmable Gate Array), or any other electronic device, system or arrangement.

Figure 5:
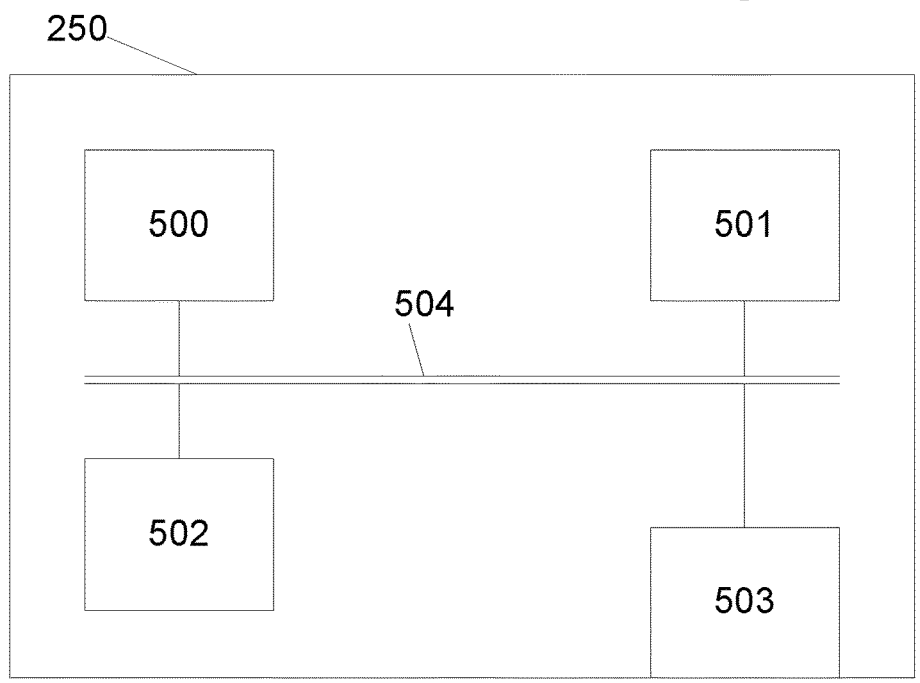
FIG. 5 is a schematic diagram of an example of a server.

An example of a suitable server 250 is shown in FIG. 5. In this example, the server includes at least one microprocessor 500, a memory 501, an optional input/output device 502, such as a keyboard and/or display, and an external interface 503, interconnected via a bus 504 as shown. In this example the external interface 503 can be utilised for connecting the server 250 to peripheral devices, such as the communications networks 240, databases 251, other storage devices, or the like. Although a single external interface 503 is shown, this is for the purpose of example only, and in practice multiple interfaces using various methods (eg. Ethernet, serial, USB, wireless or the like) may be provided.

In use, the microprocessor 500 executes instructions in the form of applications software stored in the memory 501 to allow the required processes to be performed, including communicating with the client devices 330, and optionally receiving, analysing and/or displaying results of impedance measurements. The applications software may include one or more software modules, and may be executed in a suitable execution environment, such as an operating system environment, or the like.

Accordingly, it will be appreciated that the server 250 may be formed from any suitable processing system, such as a suitably programmed client device, PC, web server, network server, or the like. In one particular example, the server 250 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement. Accordingly, whilst the term server is used, this is for the purpose of example only and is not intended to be limiting.

Whilst the server 250 is a shown as a single entity, it will be appreciated that the server 250 can be distributed over a number of geographically separate locations, for example by using processing systems and/or databases 251 that are provided as part of a cloud based environment. Thus, the above described arrangement is not essential and other suitable configurations could be used.

Figure 14:
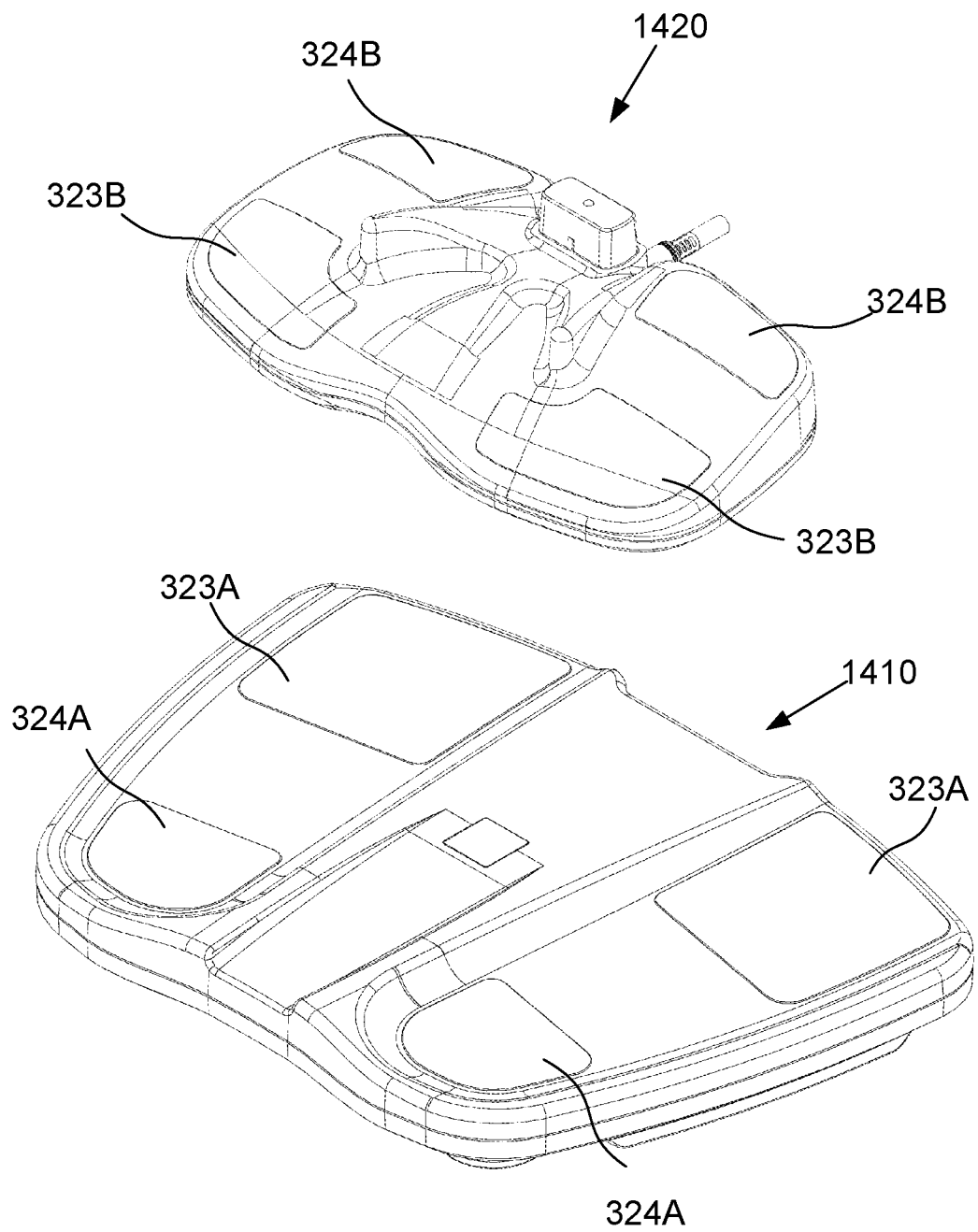
FIG. 14 is a schematic perspective view of an example of a measuring device housing; and, FIG. 15 is a flowchart of an example of a method for treating a heart failure disease state in a biological subject.

An further example of a physical construction of the measuring device is shown in FIG. 14.

In this example, the measuring device includes first and second housings 1410, 1420. The first housing 1410 includes two spaced pairs of foot drive and sense electrodes 323A, 324A, which are typically made of spaced apart metal plates provided on an upper surface of the first housing 1410, thereby forming footplates on which a user can stand.

The second housing 1420 includes two spaced pairs of hand drive and sense electrodes 323B, 324B formed from spaced apart metal plates provided on an upper surface, thereby forming handplates on which a user can rest their hands. In one embodiment the palm of the hands rests on the drive electrodes 323B with the fingers resting on the sense electrodes 324B. In one example, the device performs tetrapolar impedance measurements using the first and second housings 1410, 1420.

This arrangement allows the unit to be used by having the user stand on the first housing, or alternatively sit on a chair, with their feet resting on the foot drive and sense electrodes. The user can then place their hands on the hand drive and sense electrodes on second housing, which can be supported by a desk or table in a seated arrangement, or by a stand or other support for a standing arrangement.

The use of two housing containing separate electrodes, therefore allows impedance measurements to be performed in a variety of circumstances, and in particular allows measurements to be performed in either seated or standing arrangements, which is important in ensuring the system can be used by individuals having restricted physical capabilities. Additionally, the use of metal plate electrodes provided in a housing allows the system to be readily used, and avoids the need for preparation, such as cleaning of tissue surfaces or removal of hair, to allow wet electrodes to be applied to the skin.

Figure 6A:
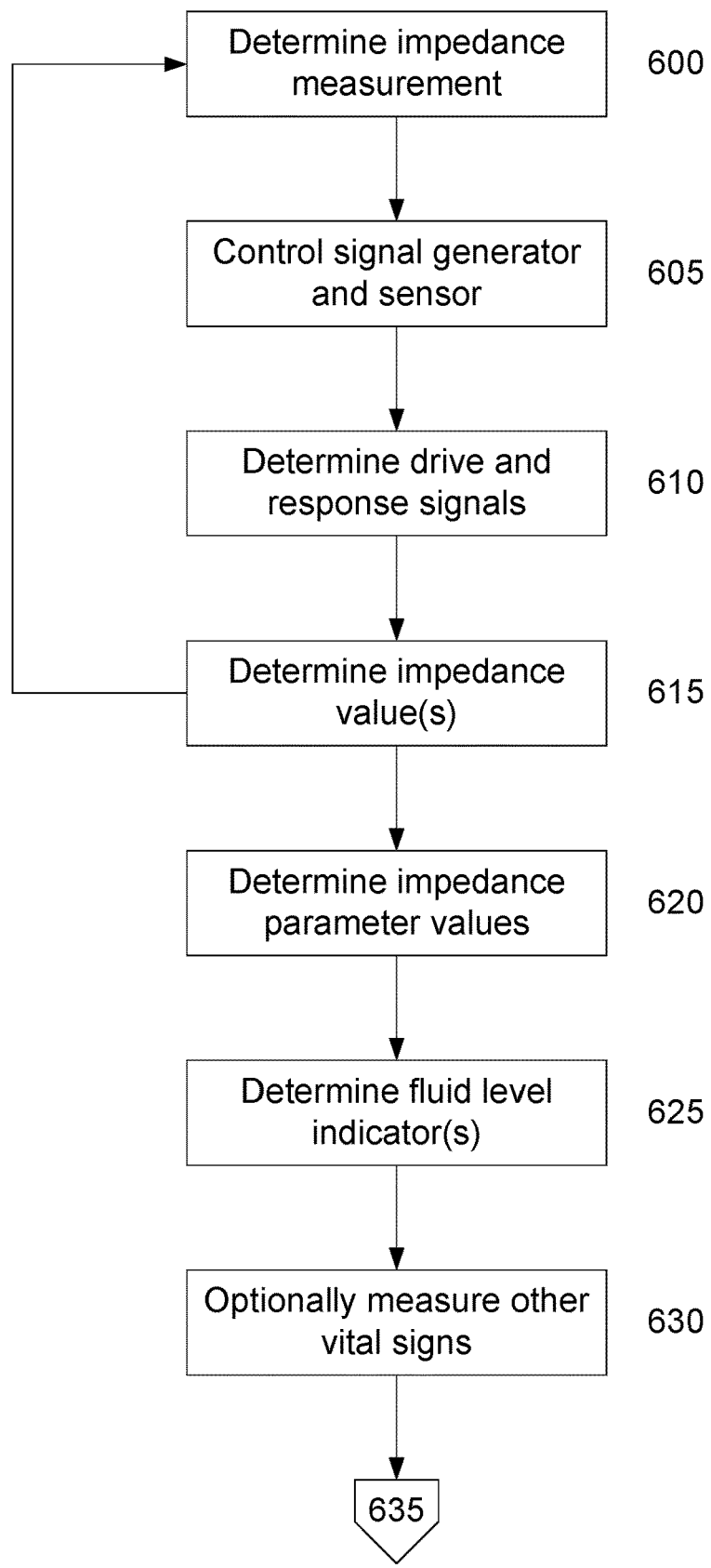
FIGS. 6A and 6B are a flowchart of a specific example of a method for determining a heart failure indicator.
Figure 6B:
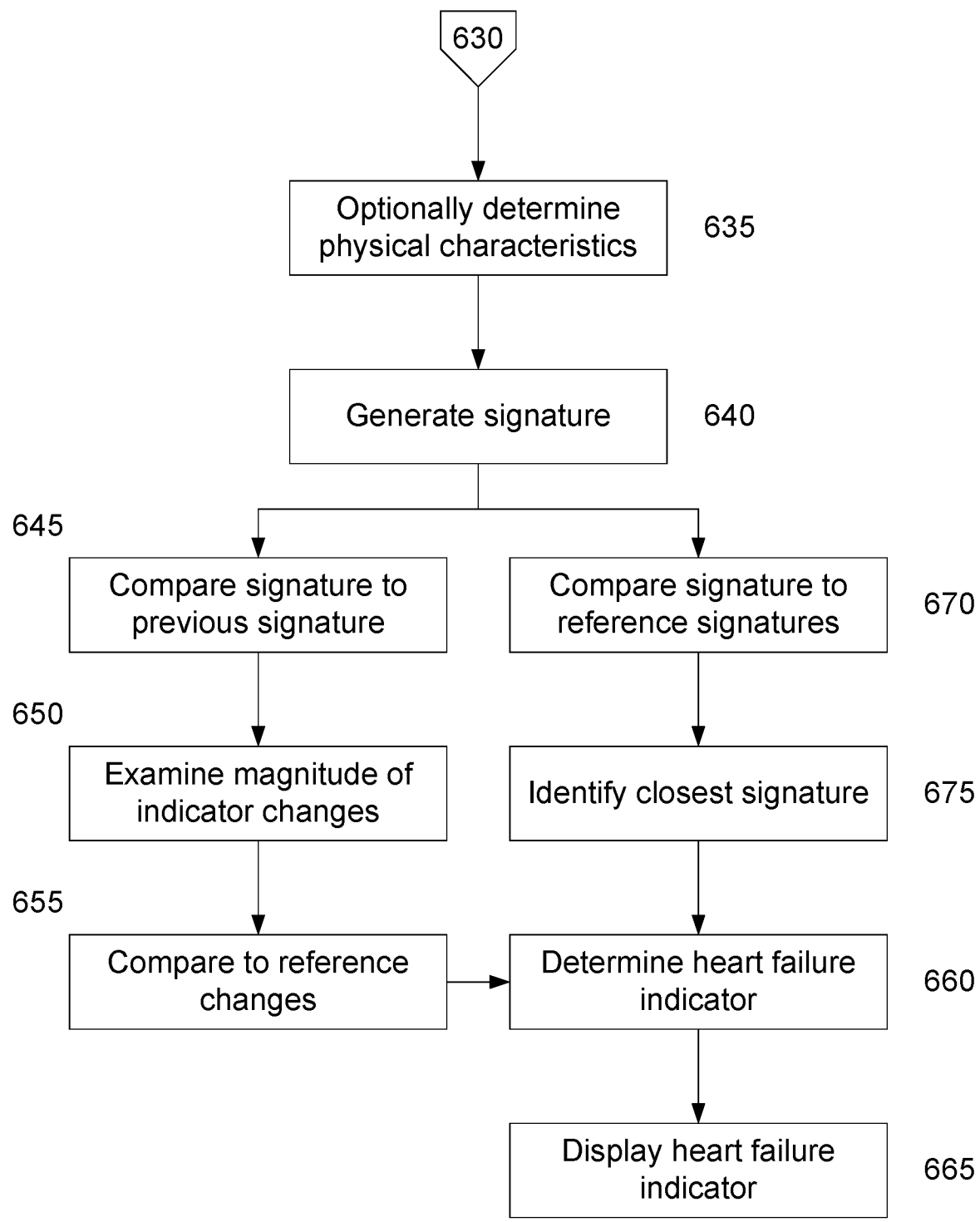

Operation of the system will now be described in further detail with reference to FIGS. 6A to 6B.

For the purpose of these examples it will also be assumed that users use the client devices 330 to control the measuring device 310 and any characteristics sensors, allowing impedance measurements to be performed and optionally allowing information regarding physical characteristics to be collected. This is typically achieved by having the user interact with the system via a GUI (Graphical User Interface), or the like presented on the client device 330, which may be generated by a local application, or hosted by the server 250, which is typically part of a cloud based environment, and displayed via a suitable application, such as a browser or the like, executed by the client device 330. Actions performed by the client device 330 are typically performed by the processor 400 in accordance with instructions stored as applications software in the memory 401 and/or input commands received from a user via the I/O device 402. Similarly, actions performed by the server 250 are performed by the processor 500 in accordance with instructions stored as applications software in the memory 501 and/or input commands received from a user via the I/O device 502, or commands received from the client device 330.

The system utilises multiple measuring and client devices 310, 330, which interact with one or more central servers 250, typically forming part of a cloud based environment. This allows reference and subject data to be collected from a number of different sources, and then aggregated and analysed centrally.

However, it will be appreciated that the above described configuration assumed for the purpose of the following examples is not essential, and numerous other configurations may be used. It will also be appreciated that the partitioning of functionality between the measuring device 310, client devices 330, and servers 250 may vary, depending on the particular implementation.

In this example, at step 600, the measuring device processor 312 determines the impedance measurement to be performed. This can be achieved in any suitable manner, but would typically include having the user selecting one of a number of available measuring procedures presented on the client device 330, with the client device 330 generating instructions which are provided to the measuring device processor 312.

Prior to a measurement being performed, the first and second electrodes 323, 324 are positioned on the subject to allow one or more signals to be injected into the subject S, and allowing a response signal to be measured. The location of the electrodes 323, 324 will depend on the segment of the subject S under study. Thus, for example, the electrodes 323, 324 can be placed on the thoracic and neck region of the subject S to allow the impedance of the chest cavity to be determined. Alternatively, positioning electrodes on the wrist and ankles of a subject allows the impedance of limbs, torso and/or the entire body to be determined. In one example, the general arrangement is to provide electrodes on the hand at the base of the knuckles and between the bony protuberances of the wrist, and on the feet at the base of the toes and at the front of the ankle.

Figure 2:
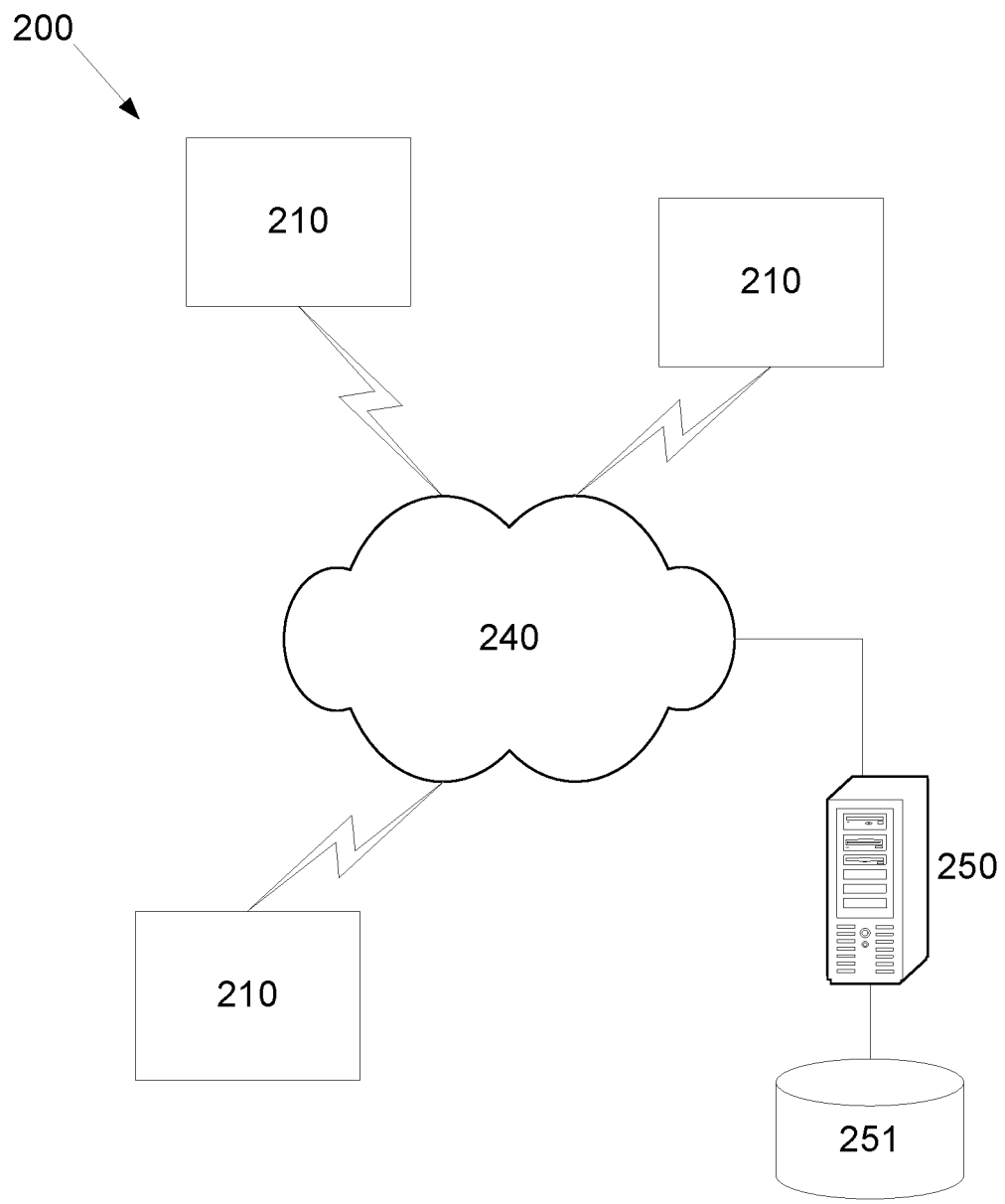
FIG. 2 is a schematic diagram of an example of a distributed system architecture for use in determining a heart failure indicator indicative of a heart failure state in a biological subject.

In an alternative arrangement using a measuring device such as shown in FIG. 2, prior to the measurement being performed the subject stands on the first housing 1410, or alternatively sits on a chair, with their feet resting on the foot drive and sense electrodes 323A, 324A. The user then places their hands on the hand drive and sense electrodes 323B, 324B on the second housing 1420, which can be supported by a desk or table in a seated arrangement, or by a stand or other support for a standing arrangement.

Figure 8A:
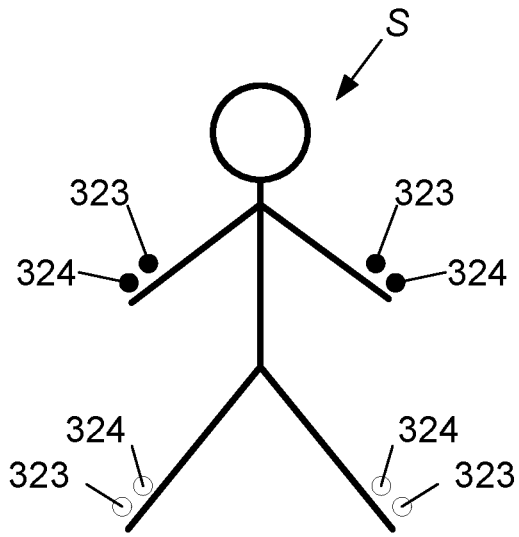
FIGS. 8A to 8E are schematic diagrams of examples of electrode positions for use in performing impedance measurements.
Figure 8B:
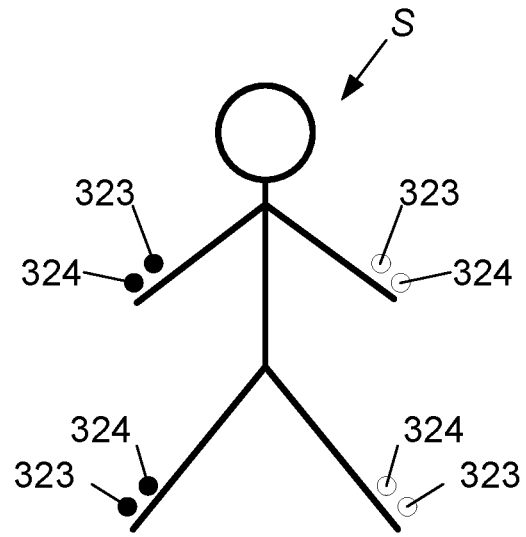
Figure 8C:
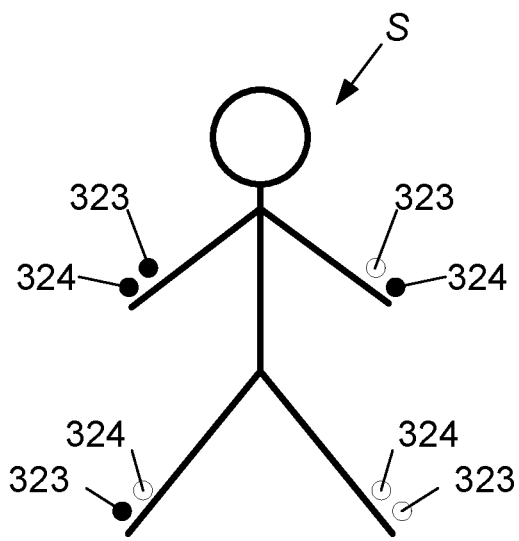
Figure 8D:
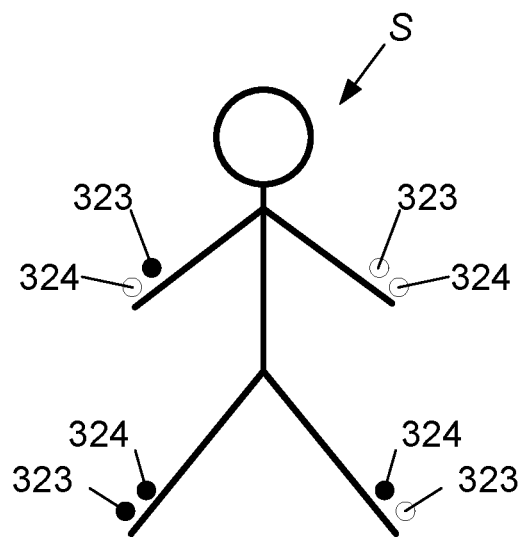
Figure 8E:
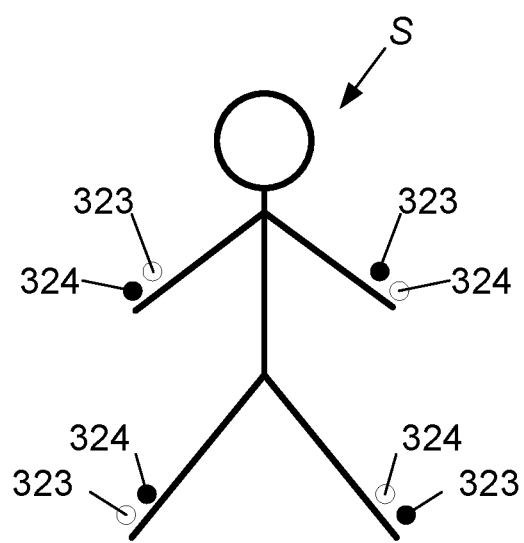

The configuration shown in FIG. 8A can then be used to allow torso measurements to be performed, whilst the configurations shown in FIGS. 8B, 8C, 8D and 8E can be used to allow right whole of body, right arm, right leg and left torso to be measured respectively. Once electrodes are positioned, the operator activates the impedance measurement process, causing a sequence of drive signals to be applied to the subject at multiple frequencies.

At step 605, the measuring device processor 312 controls the signal generator and sensor, causing the drive signals to be applied to the individual/subject and causing the corresponding response signals to be measured, allowing the measuring device processor 312 to determine both the drive and response signals at step 610.

In this regard, the response signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFI) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

At step 615, the drive and response signals are used to determine an impedance indicator, such as an impedance value, or impedance parameter value. This can be performed by the measuring device 310 alone, but more typically is performed in conjunction with the client device 330, with the measuring device providing an indication of measured impedance values to the client device 330, which then analyses these to determine the fluid level indicators.

For example, in the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined.

The above described process can be performed multiple times, for example to allow impedance measurements to be determined for multiple body segments, including the torso and one or more other segments, such as limbs. Additionally or alternatively, the process may be performed multiple times for the same body segment, with an average (or other statistical measure, such as median, mode, or the like) of two or more measurements being determined and, for example, used for further analysis.

Whilst the measured impedance can be used directly, in one example, the measured impedance is used to derive one or more impedance parameters at step 620.

Figure 7A:
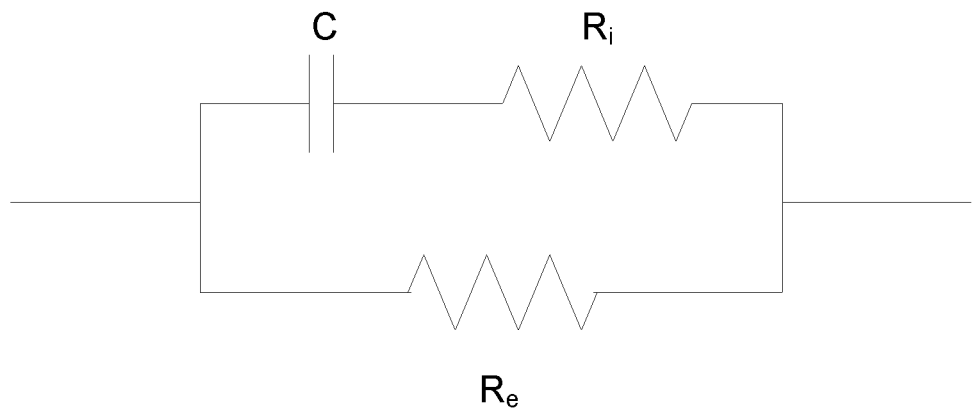
FIG. 7A is schematic diagram of an example of a theoretical equivalent circuit for biological tissue.

In this regard, FIG. 7A is an example of an equivalent circuit that effectively models the electrical behaviour of biological tissue. The equivalent circuit has two branches that represent current flow through extracellular fluid and intracellular fluid, respectively. The extracellular fluid component of biological impedance is represented by an extracellular resistance $R_e$, whilst the intracellular fluid component is represented by an intracellular resistance $R_i$ and a capacitance C representative of the cell membranes.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals the extracellular resistance $R_e$. At infinite frequency the capacitor acts as a perfect conductor and the current passes through the parallel resistive combination. The resistance at infinite frequency $R_\infty$ is given by:

$$R_\infty = \frac{R_e R_i}{R_e + R_i} \tag{1}$$

Hence the intracellular resistance is given by:

$$R_i = \frac{R_\infty R_e}{R_e - R_\infty} \tag{2}$$

Accordingly, the impedance of the equivalent circuit of FIG. 7A at an angular frequency ω, where ω=2π*frequency, is given by:

$$Z = R_\infty + \frac{R_0 - R_\infty}{1 + (j\omega\tau)} \tag{3}$$

where: $R_\infty$=impedance at infinite applied frequency
$R_0$=impedance at zero applied frequency=$R_e$ and,
τ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^\alpha} \tag{4}$$

where: α has a value between 0 and 1 and can be thought of as an indicator of the deviation of a real system from the ideal model.

Figure 7B:
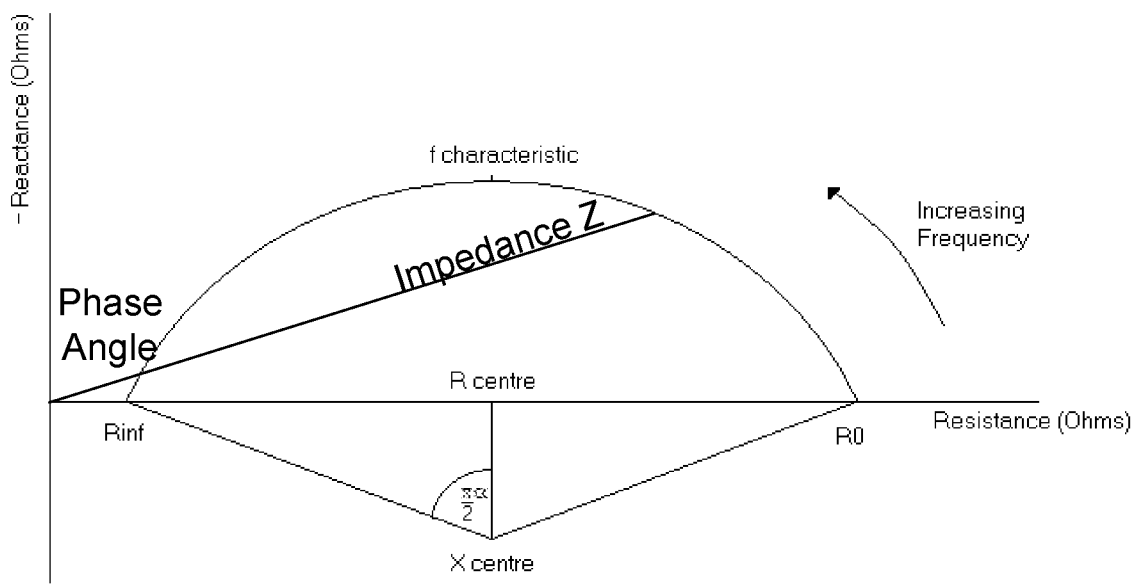
FIG. 7B is an example of a locus of impedance known as a Wessel-plot.

An example of the typical multi-frequency impedance response is shown in FIG. 7B. As frequency increases, the reactance increases to a peak at the characteristic frequency and then decreases while the resistance continually decreases. This results in a circular locus with the centre of the circle below the x axis, as shown.

Whilst the measured impedance can be used directly, in one example, the measured impedance is used to derive an impedance parameter, such as an impedance (resistance) at zero frequency, $R_0$, which equals the extracellular resistance $R_e$, or the impedance at a theoretical infinite frequency $R_\infty$, which can be used with $R_0$ to derive an intracellular resistance $R_i$, as well as other Impedance parameters. The values of impedance parameters $X_c$, $R_0$, $R_\infty$, $Z_c$ or α may be determined in any one of a number of manners such as by:
  estimating values based on impedance measurements performed at selected respective frequencies;
  solving simultaneous equations based on the impedance values determined at different frequencies;
  using iterative mathematical techniques;
  extrapolation from a plot of resistance against reactance for impedance measurements at a plurality of frequencies (a "Wessel plot" similar to that shown a in FIG. 3B);
  performing a function fitting technique, such as the use of a polynomial function.

For example, the Wessel plot is often used in BIS devices, which perform multiple measurements over a range of frequencies, such as from 1 kHz or 3 kHz to 1000 kHz, using 256 or more different frequencies within this range. A regression procedure is then used to fit the measured data to the theoretical semi-circular locus, allowing values for $X_c$, $R_0$, $R_\infty$, $Z_c$ or α to be calculated. Alternatively, a circle fitting technique can be used in which three simultaneous equations representing the geometric relationships between points on a circle are solved to allow calculation of the radius (r) and the co-ordinates of the centre of the circle (i, j) as the three parameters which define the circle.

In one example, the frequencies used are in the range 0 kHz to 1000 kHz, and in one specific example, four measurements are recorded at frequencies of 25 kHz, 50 kHz, 100 kHz, and 200 kHz, although any suitable measurement frequencies can be used.

A further alternative for determining impedance parameter values such as $X_c$, $R_0$, $R_\infty$, $Z_c$ or α is to perform impedance measurements at a single frequency, and use these as an estimate of the parameter values. In this instance, measurements performed at a single low frequency (typically less than 50 kHz) can be used to estimate $R_0$, measurements at a single high frequency (typically more than 100 kHz) can be used to estimate $R_\infty$, allowing a value of $R_i$ to be determined using equation (2) above.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

When performing measurements of cardiac and/or respiratory parameters, the system is typically used passively, with signals being measured via the sense electrodes 324 and optionally also via the drive electrodes 323. The detected signals are a superposition of voltages generated by the human body, and will include cardiac and respiratory components, which can typically be isolated through suitable filtering, for example 1-40 Hz for cardiac signals and below 1 Hz for respiratory signals.

In any event, it will be appreciated that any suitable technique for determination of the parameter values such as $R_0$, $Z_c$, $R_\infty$, and $X_c$ may be used, hence allowing $R_i$ to be derived.

Moreover, the total body water (TBW) may be determined from impedance parameters associated with the subject's whole body by:

$$TBW = R_e' + R_i' \qquad (5)$$

where: TBW=total body water
$R_e'$=volume of extracellular fluid of whole body
$R_i'$=volume of intracellular fluid of whole body In any event, at step 625, the client device 330 determines one or more fluid level indicators using the impedance parameter values. In particular, the client device 330 will use the impedance parameter values to calculate fluid level indicators, such as intracellular or extracellular fluid levels, and/or a ratio of intracellular to extracellular fluid levels, with this being performed for the torso and optionally for other body segments. Similarly, the fluid level indicators could include relative indicators based on differences in fluid level indicators for the torso and other body segments, for example by calculating a ratio of torso to limb fluid indicators.

At step 630, one or more vital signs and/or one or more other body parameters could optionally be measured, with the results of these measurements being used to determine vital signs indicators and/or other subject body parameter values. This could be performed manually, for example by having a clinician manually input measurement values using an interface presented on the client device 330, or could be performed by having the client device acquire measurements from suitable vital signs sensors and/or other body parameter sensors.

At step 635, the client device 330 optionally determines physical characteristics of the individual. Again, this could be achieved by manual input via a user interface and/or by receiving data from the sensing device 320.

At step 640, the client device 330 generates a signature, which is then either analysed locally by the client device 330, or transferred to the server 250 for analysis, depending on the preferred implementation. The signature can be of any appropriate form, and could include a single fluid level indicator, but more typically includes a plurality of different fluid level indicators, and optionally other subject body parameter values and/or vital signs indicators, and may be provided in the form of a multi-dimensional vector. The signature can be provided together with information regarding physical characteristics of the subject, assuming this is transferred to a server 250 for analysis.

At step 645, the server 250 or client device 330 compares the signature to a previous signature for the subject. This is performed in order to identify a magnitude and direction of any changes in fluid levels for the subject. For example, this can be performed to determine if the fluid levels in any individual body segments have increased or decreased, and if so by how much, and/or to determine if there is any change in relative fluid levels between the torso and other body segments, for example to determine if torso fluid levels have increased relative to limb fluid levels.

The changes are then compared to reference changes at step 655, which represent threshold values corresponding broadly to a change that has clinical significance, representing either an onset or clinical worsening/improving of a heart failure state. The threshold values can be established based on studies of individuals having heart failure, by monitoring changes in health state observed for different fluid level changes.

At step 660, results of the comparison are used to generate a heart failure indicator, with this optionally being displayed at step 665. In this regard, the heart failure indicator could be of any appropriate form and could include for example, a percentage likelihood or heart failure state score indicative of the likelihood of the subject having each of one or more heart failure states. Thus, this could be a numeric value scaled between 1 and 10, with 1 indicative of a low likelihood and 10 a high likelihood or vice versa. Additionally, or alternatively this could be presented as a graphical representation, for example using a pointer and scale to indicate the likelihood of the subject having a condition, or could include information regarding results of the comparison, allowing a medical practitioner to understand the outcome of the analysis and how any indicator has been determined, which can facilitate a identification process.

Additionally and/or alternatively, the subject signature can be compared to one or more reference signatures at step 670, for example by comparing to reference signatures derived from reference individuals having different heart failure states and similar physical characteristics to the subject.

In this regard, reference signatures are determined by measuring fluid levels and physical characteristics and optionally other vital signs and/or other body parameters for reference individuals. The individuals are allocated to a respective group based on any heart failure states identified for the individual, so as to define groups of individuals for each of a plurality of different heart failure states. Each group is then further divided into sub-groups based on physical characteristics of the individuals, so that groups exist for different heart failure states for each of a particular group of physical characteristics.

It will be appreciated that the manner in which this division occurs can vary depending on a number of factors, including the preferred implementation, the particular physical characteristics, the heart failure state or the like. For example, individuals could be allocated to different groups based on one or more of die individual's sex, etllticity, age, weight or height. Thus, for example, a number of sub-groups could be defined for particular ranges of age, weight and height, with the individual being allocated to the group as appropriate according to their physical characteristics.

Additionally, it is possible for multiple different overlapping sub-groups to be created for different combinations. For example, a respective group could be formed for all male and all female individuals, with separate additional groups being formed for male/female individuals of particular age ranges, meaning that individuals can be allocated to multiple sub-groups.

It will also be appreciated that the groups formed may differ depending on the respective heart failure state. For example, a low prevalence of some heart failure states in young people may mean that groups for that heart failure state will span a larger age range than for other heart failure states.

Once the comparison has been performed, the closest reference signature or group is identified at step 675, with this being used to determine the heart failure indicator.

The above described processes can be performed in parallel, for example to assess a severity of heart failure by comparison to the reference signatures and to find out if the condition is worsening or improving by comparison to previous signatures for the subject.

In any event, it will be appreciated that the above described process can assist medical personnel in performing an identification and/or treating a subject.

Figure 9:
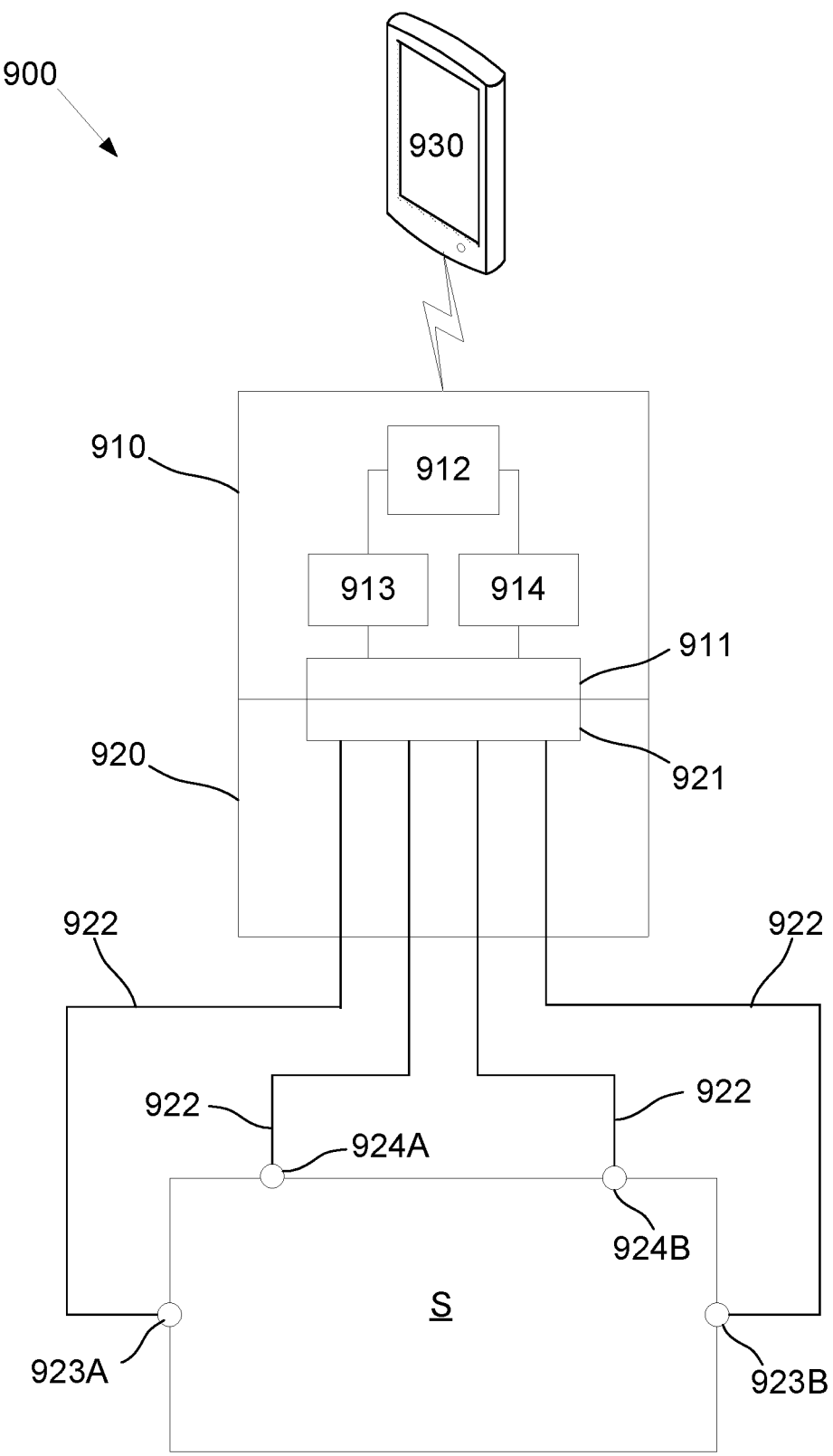
FIG. 9 is a schematic diagram of an example of an impedance measuring system.

The above described process has been described as being performed using a measuring unit including a measuring device 310 coupled directly to electrodes. However, alternative arrangements can be used and a further example of a measuring unit will now be described with reference to FIG. 9.

In this example, the measuring unit is similar to that described above with respect to FIG. 3, and similar features will not therefore be described in detail. However, in this example, the measuring unit includes a measuring device 910 including a first connector 911 electrically connected to at least the at least one sensor 914 and the at least one signal generator 913, and a separate connectivity module 920, including a connectivity module housing and a second connector 921 electrically connected to the electrodes 923, 924.

In use the measuring device 910 is connected to the connectivity module 920 by interconnecting the first and second connectors 911, 921 so first electrodes 923 are electrically connected to the at least one signal generator and second electrodes 924 are electrically connected to the at least one sensor, thereby allowing a drive signal to be applied to the subject via the first electrodes 923 (referred to generally as drive electrodes) and allowing the response signal to be measured via the second electrodes 924 (referred to generally as sense electrodes) so that the at least one impedance measurement can be performed.

In the above described arrangement, a separate measuring device 910 and connectivity module 920 are used, allowing a single type of measuring device 910 to be configured for use with multiple different types of connectivity module 920. This in turn enables a range of different impedance measurements to be performed using different configurations of connectivity module. In this regard, different electrode arrangements 923, 924 may be required for performing different types of impedance measurement, and so the provision of a common measuring device, and different types of connectivity module allows a single measuring device to be used in a wider range of circumstances than would be possible for a single integrated device.

For example, the connectivity module 920 could include stand-on plates and hand grip electrodes for use in measuring aspects of a subject's body composition, whilst adhesive electrodes positioned on the wrist and ankles might be preferred for oedema detection, or the like. In this instance, by allowing a common measuring device to be selectively connected to different connectivity modules, this allows the most suitable electrode configuration to be used, whilst allowing a common measuring device design to be used, which can reduce overall hardware requirements and allow for greater efficiencies in manufacture.

Furthermore, in one example, the measuring device 910 can be adapted to sense the type of connectivity module 920 to which it is connected, thereby at least partially controlling the impedance measurement process based on the connectivity module currently being used.

Figure 10:
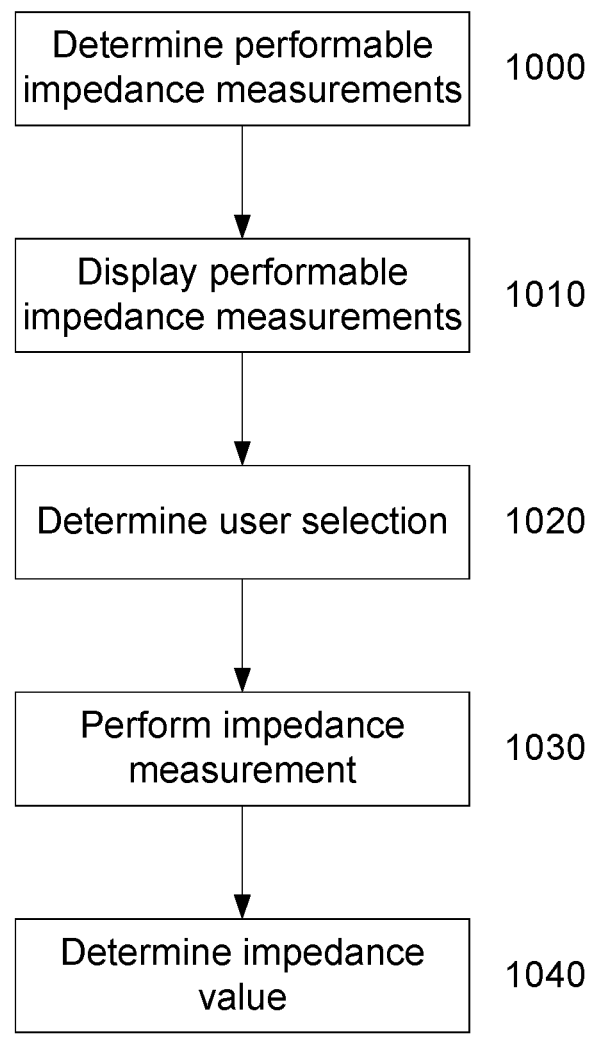
FIG. 10 is a flowchart of an example of an impedance measuring process.

An example of this, will now be described with reference to FIG. 10.

In this example, at step 1000, the measuring device processor 912 determines a connectivity module type. This can be achieved in any suitable manner, depending on the preferred implementation and could be based on a configuration of connections between the connectors 911, 921, electrical characteristics or properties of components within the connectivity module, stored identifiers, or the like.

At step 1010, the connectivity module type is used to determine the impedance measurements that can be performed using the respective connectivity module 920. This can be performed by the measuring device processor 912, or alternatively could be performed by a client device 930 in communication with the measuring device processor 912. In any event, different connectivity module types could be associated with respective types of impedance measurement, for example based on the configuration of electrodes and/or any other components provided therein, such as voltage/current buffers or the like. Thus, information regarding the connectivity module type can be used to determine the impedance measurements that can be performed, allowing operation of the system to be controlled accordingly.

Prior to a measurement being performed, the first and second electrodes 923, 924 are positioned on the subject to allow one or more signals to be injected into the subject S, and allowing a response signal to be measured.

Once positioned, at step 1020, the measuring device processor 912 controls the at least one signal generator 910 and the at least one sensor 911, allowing the impedance measurements to be performed at step 1030, with impedance values being determined at step 1040.

Figure 11A:
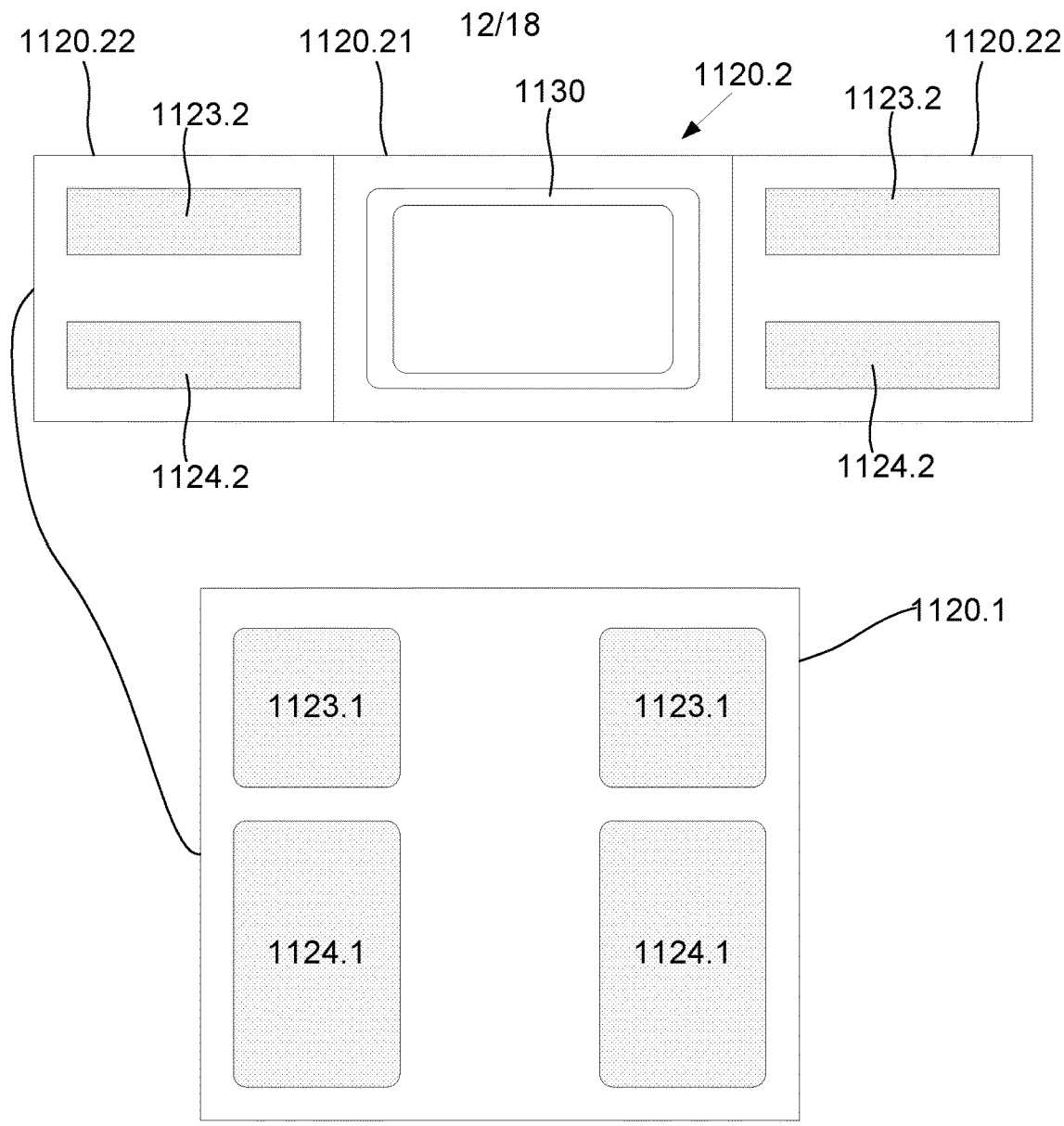
FIG. 11A is a schematic diagram of a specific example of an impedance measuring system.
Figure 11B:
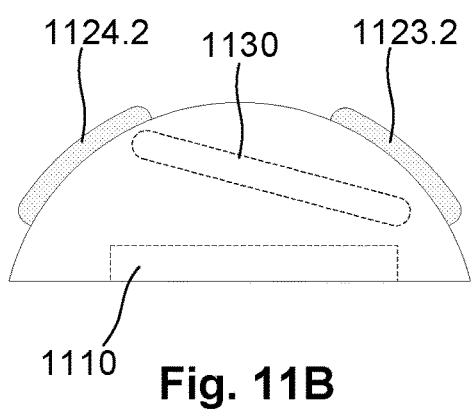
FIG. 11B is schematic end view of a second housing of the connectivity module of FIG. 11A.

A specific example connectivity module is shown in FIGS. 11A and 11B.

In this example, the connectivity module 1120 includes first and second housings 1120.1, 1120.2. The first housing 1120.1 has a form factor similar to a set of scales, and includes two spaced pairs of foot drive and sense electrodes 1123.1, 1124.1 forming footplates, or laminar electrode sheets, on which a user can stand. The second housing 1120.2 is an elongate housing having three portions along its length, with a central rectangular portion 1120.21 positioned between two outer semicylindrical portions 1120.22. In this example, the outer semicylindrical portions 1120.22 support curved electrode plates 1123.2, 1124.2 or electrode sheets, mounted on opposing sides of the body allowing the user to place their palms and fingers on the plates 1123.2, 1124.2. In this regard, the curvature of the surface assists with comfort and ensures good physical and hence electrical contact between the user's hands and the electrodes. Meanwhile the central portion can be used to support the measuring device 1110, and also optionally a client device 1130, such as a tablet or the like, which can be used to control the measurement process as will be described in more detail below.

It will be appreciated however that a wide variety of connectivity modules could be provided, with these being used in different circumstances to allow respective types of impedance measurement to be performed, whilst still using a common measuring device.

Figure 12A:
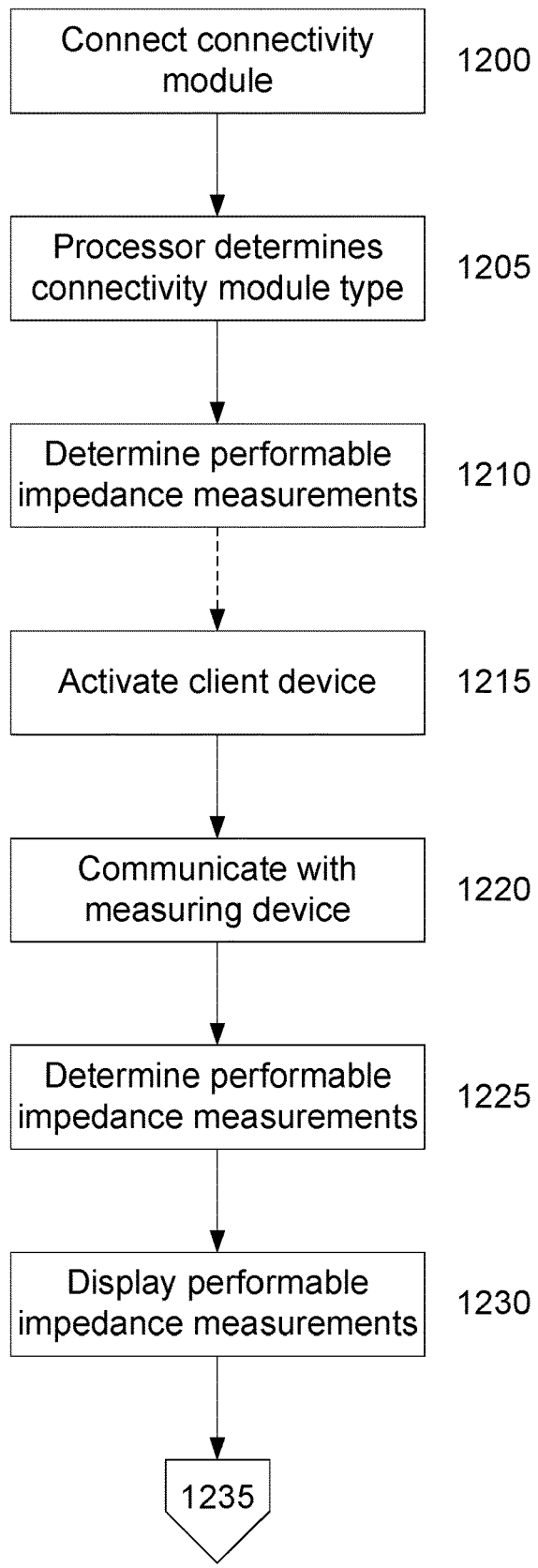
FIGS. 12A to 12C are a flowchart of a further example of an impedance measuring process.
Figure 12B:
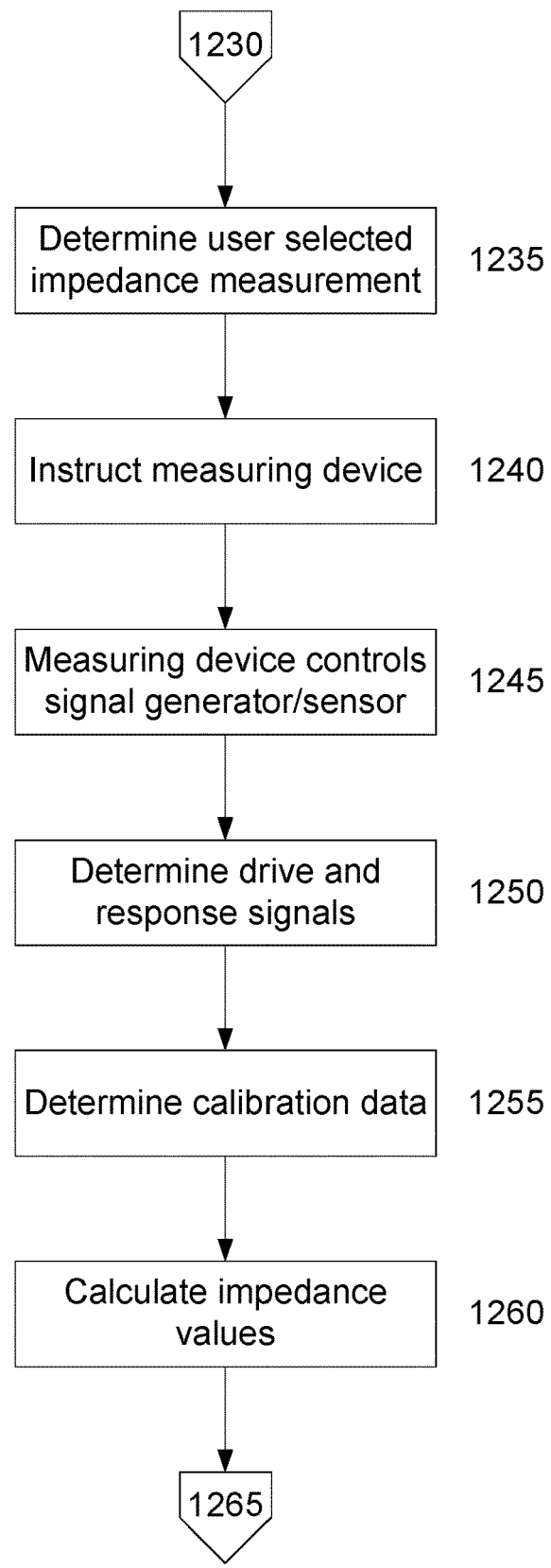
Figure 12C:
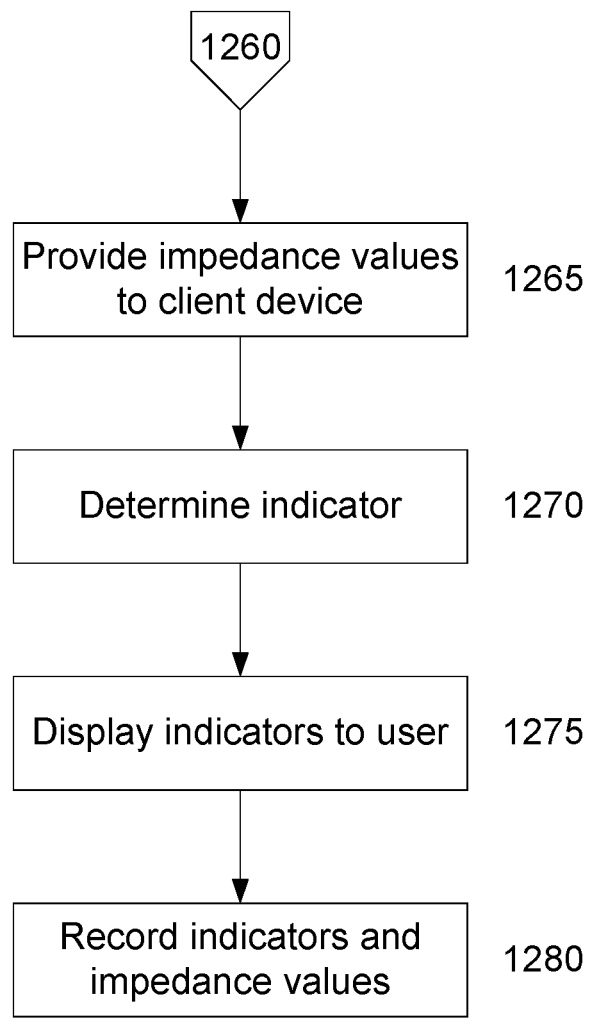

A further example of an impedance measurement process will now be described with reference to FIGS. 12A to 12C.

In this example, at step 1200 the measuring device 910 is initially connected to a connectivity module 920, and activated, causing the measuring device processor 912 to determine a connectivity module type of the connectivity module 920 at step 1205. This is typically performed by having the measuring device processor 912 determine a connectivity module identifier or the like, allowing the measuring device processor to determine performable impedance measurements at step 1210. In this regard, the measuring device 910 can store a list of performable impedance measurements that can be performed for each type of module in onboard memory, allowing an indication of performable impedance measurements to be retrieved based on the connectivity module type. However, alternatively, the connectivity module type could be provided to the client device 930, allowing this to be performed by the client device 930.

At step 1215, the client device 930 is activated, with relevant software being activated, allowing the client device 930 to commence communicating with the measuring device 910 at step 1220. As part of this process, the measuring device and client device may need to be paired, for example undergoing a Bluetooth pairing process, or the like, depending on the manner in which the client device 930 and measuring device communicate. Alternatively a particular measuring device 910 previously paired with the client device 930 may need to be identified from a list of available devices, as will be appreciated by persons skilled in the art.

At step 1225, the client device 930 determines the performable impedance measurements from the measuring device 910, or receives an indication of the connectivity module type, allowing the performable impedance measurements to be determined locally. In any event, an indication of the performable impedance measurements is then displayed to a user at step 1230, for example in the form of a list of impedance measurement processes.

The user selects a performable impedance measurement at step 1235, causing the client device 930 to instruct the measuring device 910 to perform the impedance measurements at step 1240. This can include providing the measuring device 910 with an indication of particular impedance measurements to be performed, or could include providing instructions regarding the control of or settings for the signal generator, sensor and any switches. Additionally and/or alternatively, this could include uploading soft or firmware to the measuring device, allowing the measuring device 910 to operate as required.

At step 1245, the measuring device processor 912 controls the signal generator/sensor 910, 911, determining corresponding drive and response signals, applied or measured via respective drive and sense electrodes 923, 924, at step 1250. The measuring device processor 912 then determines calibration data at step 1255, with this typically being stored locally and accessed based on either the connectivity module type and/or connectivity module identifier. In this regard each type of connectivity module will typically have different electrical properties and these will need to be taken into account when performing impedance measurements. This is achieved by measuring drive and response signals for standardised electrical components with this then being used to generate calibration data which can be used in calculating impedance measurements. This could be performed for each type of module, and/or for each individual connectivity module, depending for example of the level of accuracy required for the calculated impedance values.

In any event, the calibration data is used together with the indication of the drive and corresponding response signals to calculate impedance values at step 1260, for example by modifying the measured drive and response signals to take into account device characteristics, and then using the modified signals to calculate the impedance.

Once impedance values have been calculated for each measurement performed, an indication of the impedance values being provided to the client device 930 at step 1265, allowing these to be used by the client device to determine one or more indicators at step 1270. This process can involve calculating impedance parameter values, such as $R_0$, $R_\infty$, or the like and then using these values to determine indicators, such as fluids levels including levels of extracellular and intracellular fluid, body composition parameters, such as fat free mass, or the like.

The determined indicator(s) and/or impedance values can then be displayed to the user at step 1275, via a suitable user interface with the indicators and impedance values being optionally stored at step 1280, for example by transferring these to the server 250 for storage in the database 251.

Accordingly, it will be appreciated that the above described arrangement allows the impedance measurement procedure to be controlled via a client device, such as a smartphone or tablet. This allows general processing of impedance measurements and control of the system to be performed using generic hardware, without unduly adding to the cost of the impedance measuring system.

In the above described arrangements, a single configuration of measuring device is adapted to be used with connectivity modules that provide onward connectivity to the subject. Different types of connectivity module can be used with the same measuring device, with the nature of the connectivity module being used to control the impedance measuring processes that can be performed. This allows a user to obtain a single measuring device and then use this with different connectivity modules, allowing different measurements to be performed. This reduces die complexity of the measuring device, and allows a single configuration of measuring device to be used in wide range of scenarios. Additionally, this allows users to only acquire connectivity modules that are relevant to measurements that are to be performed, avoiding the need to acquire unnecessary hardware. Finally, this also allows the connectivity modules to be customised for the particular measurements that are to be performed, which in turn helps ensure the electrode configuration is optimised for the particular measurements being performed.

In the above described arrangements, the measuring device is provided in a measuring device housing that is separate to the connectivity module housing. This is beneficial in terms of facilitating use of a single measuring device with multiple different connectivity modules, particularly in terms of allowing for measuring device handling to be performed when attaching or detaching the measuring device and connectivity modules, without potential to damage components of the measuring device.

However, it will be appreciated that this is not essential, and alternatively, the measuring device could be provided within the connectivity module housing, and hence not require a separate measuring device housing. In this instance, the connectivity module housing could include a door, cover, lid or other opening, that provides access to the inside of the connectivity module, and the second connector provided therein. This allows the measuring device to be inserted into the connectivity module housing and coupled to the second connector, in a manner substantially similar to that described above, albeit with the measuring device contained entirely within the connectivity module housing.

For example, the measuring device could include a circuit board, having the relevant components and first connector mounted thereon. This could be supported internally within the connectivity module, either through physical engagement between the first and second connectors, or through cooperation with a separate bracket or other mounting. Thus, it will be appreciated that this arrangement could be analogous to the manner in which a card, such as a graphics card or RAM is installed in a computer system housing through attachment to a motherboard, with the measuring device corresponding to the card, and the connectivity module the computer system and motherboard.

In this latter arrangement, it would be typical although not essential for the measuring device to be mounted in a single connectivity module, as opposed to being used interchangeably with different connectivity modules, to thereby ensure components of the measuring device are not damaged. Nevertheless, this would still allow for common measuring devices to be used with a wide range of different connectivity modules, thereby reducing manufacturing complexity and requirements, whilst still allowing a wide range of functionality to be achieved.

Accordingly, it will be appreciated that the above described approach allows impedance measurements to be used in a manner akin to other vital signs. In particular impedance measurements can be used to enable or facilitate diagnosis of a wide range of different heart failure states.

This could be performed independently, but is more typically performed in conjunction with measurement of other vital signs and/or other subject body parameters to provide enhanced discriminatory capabilities.

Whilst this could be performed in an ad-hoc manner, more preferably this is achieved using a standardised approach performed in a range of different locations and circumstances, allowing impedance indicators to be measured for a wide variety of physical characteristics and heart failure states. The data can then be aggregated centrally and mined in order to derive reference signatures, each of which defines a combination of impedance and/or other vital sign indicators and/or other body parameters that are unique to a particular heart failure state for a given set of physical characteristics. Subsequently, impedance and optionally other vital sign indicators and/or other body parameters can be measured for subjects, and then compared to the reference signatures, allowing a likelihood of the subject having a respective heart failure state to be quantified in the form of a heart failure indicator, which can be an indication of the likelihood of the subject having one or more heart failure states. This information can then be used by clinicians, in order to assist clinicians in making a clinical diagnosis of heart failure states.

It will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. A system for determining a heart failure indicator indicative of a heart failure disease state in a biological subject, the system including:
   a) at least one signal generator coupled to first electrodes provided in electrical contact with the subject in use, the at least one signal generator being adapted to generate a drive signal;
   b) at least one sensor coupled to second electrodes provided in electrical contact with the subject in use, the at least one sensor being adapted to measure a response signal; and,
   c) at least one processing device that:
      i) at least in part controls the at least one signal generator and receives an indication of a measured response signal from the at least one sensor, allowing impedance measurements to be performed across at least one body segment of the subject, the at least one body segment including at least
         a limb of the subject, and
         a torso of the subject;
      ii) determines a fluid level indicator using first impedance values obtained by performing impedance measurements across the at least one body segment of the subject at a first time, wherein the first fluid level indicator is a ratio of extracellular fluid levels to total body water in the at least one body segment;
      iii) determines a second fluid level indicator using second impedance values obtained by performing impedance measurements across the at least one body segment of the subject at a second time, wherein the second fluid level indicator is a ratio of extracellular fluid levels to total body water in the at least one body segment; and,
      iv) determines a heart failure indicator by:
         (1) using the first and second fluid level indicators to determine a fluid level change using a difference between the first and second fluid level indicators; and
         (2) using the fluid level change to determine the heart failure indicator, wherein the heart failure indicator is indicative of at least one of:
            a presence, absence, degree or severity of heart failure;
            a likelihood the subject has heart failure;
            a prognosis associated with heart failure;
            an indication of worsening heart failure; or
            an indication of cardiac decompensation.

2. A system according to claim 1, wherein the fluid level indicator is at least partially indicative of at least one of:
   a) intracellular fluid levels in the body segment;
   b) total body water;
   c) a ratio of extracellular fluid levels in the body segment to total body water;
   d) a ratio of extracellular to intracellular fluid levels in the body segment; and,
   e) a ratio of intracellular to extracellular fluid levels in the body segment.

3. A system according to claim 1, wherein the at least one processing device determines the heart failure indicator using the first and second fluid level indicators by at least one of:
   a) determining a rate of change of the fluid level change and determining the heart failure indicator using the rate of change;
   b) comparing a rate of change to at least one threshold and determining the heart failure indicator in accordance with results of the comparison;
   c) comparing a fluid level change to at least one threshold and determining the heart failure indicator in accordance with results of the comparison; and,
   d) determining a fluid level gradient using the first and second fluid level indicators and the first and second times and determining the heart failure indicator using the fluid level gradient.

4. A system according to claim 3, wherein the at least one threshold is based on at least one of:
   a) a threshold or variance established for a sample reference population; and,
   b) a time period between the first and second time.

5. A system according to claim 3, wherein the at least one processing device:
   a) compares the fluid level change to at least one absolute reference;
   b) compares the rate of change to at least one rate of change reference; and,
   c) determines the heart failure indicator in accordance with results of the comparisons.

6. A system according to claim 3, wherein the at least one processing device:
   a) determines a baseline using the first fluid level indicator;
   b) determines a plurality of second fluid level indicators by performing multiple impedance measurements at subsequent times;
   c) determines a plurality of fluid level changes using a difference in the baseline and each of the plurality of second fluid level indicators; and,
   d) determines the heart failure indicator using the plurality of fluid level changes.

7. A system according to claim 1, wherein the at least one processing device determines at least one of a degree and a severity of heart failure in accordance with the heart failure indicator.

8. A system according to claim 1, wherein the system includes a display, and the at least one processing device:
   a) generates a representation using at least one of the fluid level indicator and the heart failure indicator; and,
   b) displays the representation on the display.

9. A system according to claim 1, wherein the at least one processing device:
   a) determines at least one impedance parameter value using at least one of:
      i) an impedance value obtained by performing impedance measurements at a single frequency; and,
      ii) a plurality of impedance values obtained by performing impedance measurements at a plurality of frequencies; and,
   b) determines the fluid level indicator using the at least one impedance parameter value.

10. A system according to claim 1, wherein the at least one processing device:
   a) uses the fluid level indicator to identify a plurality of possible disease states;
   b) identifies further analysis to be performed in accordance with the identified possible disease states; and,
   c) performs the further analysis to thereby distinguish between the possible disease states and heart failure.

11. A system according to claim 1, wherein the at least one processing device:
   a) determines a signature indicative of a plurality of fluid level indicators; and,
   b) compares the signature to at least one of:
      i) a reference signature derived from a reference population; and,
      ii) a previous signature for the subject; and,
   c) determines the heart failure indicator in accordance with results of the comparison.

12. A system according to claim 1, wherein the at least one processing device:
   a) determines a signature indicative of:
      i) at least one fluid level indicator; and,
      ii) at least one other subject body parameter value obtained by performing at least one measurement on one or more other body parameters of the subject;
   b) compares the signature to at least one of:
      i) a reference signature derived from a reference population; and,
      ii) a previous signature for the subject; and,
   c) determines the heart failure indicator in accordance with results of the comparison.

13. A system according to claim 12, wherein the at least one other subject body parameter value is indicative of at least one of:
   a) a vital signs indicator;
   b) a cardiac parameter value;
   c) a respiratory parameter value;
   d) a blood potassium level;
   e) a temperature;
   f) a blood pressure;
   g) a respiratory rate;
   h) a heart rate; and,
   i) a blood oxygenation level.

14. A system according to claim 12, wherein the at least one processing device:
   a) determines selected reference signatures using subject characteristic data indicative of one or more physical characteristics of the subject;
   b) compares at least the subject impedance indicators to the selected reference signatures; and,
   c) generates the heart failure indicator at least partially in accordance with results of the comparison.

15. A system according to claim 14, wherein the at least one processing device:
   a) generates at least one subject signature indicative of the at least one fluid level indicator and at least one other subject body parameter value;
   b) compares the at least one subject signature to the selected reference signatures; and,
   c) generates the heart failure indicator based on a degree of similarity between the subject signature and the selected reference signatures.

16. A system according to claim 1, wherein the system includes a measuring unit including:
   a) the at least one signal generator coupled to the first electrodes provided in electrical contact with the subject in use;
   b) the at least one sensor coupled to the second electrodes provided in electrical contact with the subject in use; and, c) a measuring device processor that at least in part controls the at least one signal generator and receives an indication of a measured response signal from the at least one sensor, allowing the at least one impedance measurement to be performed.

17. A system according to claim 1, wherein the electrodes are mounted on a housing configured to allow the subject to position their hands in contact with the housing and thereby form an electrical contact with the first and second electrodes and the electrodes are mounted on a housing configured to allow the subject to position their feet in contact with the housing and thereby form an electrical contact with the first and second electrodes.

18. A system according to claim 16, wherein each measuring system includes a processing system in communication with the measuring unit, the processing system including the at least one processing device and being configured to:
   a) cause impedance measurements to be performed by the measuring unit; and,
   b) determine the heart failure indicator.

19. A system according to claim 18, wherein the processing system:
   a) determines an impedance measurement process to be performed, the impedance measurement process including a sequence of impedance measurements;
   b) causes the measuring unit to perform the sequence of impedance measurements;
   c) receives an indication of at least one impedance value from the measuring unit, the at least one impedance value being indicative of a measured impedance; and,
   d) generates impedance data using the at least one impedance value.

20. A method for determining a heart failure indicator indicative of a heart failure disease state in a biological subject, the method including, in at least one processing device:
   a) determining a first fluid level indicator using first impedance values obtained by performing impedance measurements across at least one body segment of the subject at a first time, wherein the first fluid level indicator is a ratio of extracellular fluid levels to total body water in the at least one body segment, the at least one body segment including at least
      a limb of the subject, and
      a torso of the subject;
   b) determining a second fluid level indicator using second impedance values obtained by performing impedance measurements across the at least one body segment of the subject at a second time, wherein the second fluid level indicator is a ratio of extracellular fluid levels to total body water in the at least one body segment; and,
   c) determining a heart failure indicator by:
      using the first and second fluid level indicators to determine a fluid level change using a difference between the first and second fluid level indicators, and
      determining the heart failure indicator using the fluid level change to determine the heart failure indicator, wherein the heart failure indicator is indicative of at least one of:
         a presence, absence, degree or severity of heart failure;
         a likelihood the subject has heart failure;
         a prognosis associated with heart failure;
         an indication of worsening heart failure; or
         an indication of cardiac decompensation.

21. A system according to claim 1, wherein the at least on processing device:
   a) controls the at least one signal generator and receives an indication of a measured response signal from the at least one sensor to periodically performing at least one impedance measurement across the at least one body segment of the subject;
   b) determines the fluid level indicator for each measurement; and,
   determines the heart failure indicator by monitoring changes in the fluid level indicator over time.

* * * * *